United States Patent
Oh et al.

(10) Patent No.: US 8,853,441 B2
(45) Date of Patent: Oct. 7, 2014

(54) SULFONIUM COMPOUND, PHOTOACID GENERATOR, AND RESIST COMPOSITION

(75) Inventors: Jung Hoon Oh, Chungcheongnam-do (KR); Dae Kyung Yoon, Chungcheongnam-do (KR); Seung Duk Cho, Chungcheongnam-do (KR); So Jeong Park, Chungcheongnam-do (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 13/557,893

(22) Filed: Jul. 25, 2012

(65) Prior Publication Data

US 2013/0035503 A1    Feb. 7, 2013

(30) Foreign Application Priority Data

Aug. 3, 2011  (KR) .................. 10-2011-0077527

(51) Int. Cl.
| | | |
|---|---|---|
| *C07C 69/013* | (2006.01) | |
| *C07C 69/017* | (2006.01) | |
| *C07C 309/02* | (2006.01) | |
| *C07C 309/39* | (2006.01) | |
| *C07C 309/44* | (2006.01) | |
| *C07C 381/12* | (2006.01) | |
| *G03F 7/00* | (2006.01) | |
| *C07C 309/12* | (2006.01) | |
| *G03F 7/004* | (2006.01) | |
| *C07D 333/46* | (2006.01) | |
| *C07C 309/06* | (2006.01) | |
| *C07D 307/64* | (2006.01) | |
| *G03C 1/00* | (2006.01) | |
| *G03F 7/039* | (2006.01) | |

(52) U.S. Cl.
CPC ............ C07C 309/06 (2013.01); C07C 381/12 (2013.01); G03F 7/00 (2013.01); C07C 309/12 (2013.01); C07C 309/02 (2013.01); G03F 7/0046 (2013.01); C07D 333/46 (2013.01); G03F 7/0045 (2013.01); C07C 2102/42 (2013.01); C07C 2103/74 (2013.01); G03F 7/0397 (2013.01); C07D 307/64 (2013.01); G03F 7/0395 (2013.01); G03F 7/004 (2013.01)
USPC ............... 560/138; 562/30; 562/42; 562/109; 562/113; 430/270.1

(58) Field of Classification Search
CPC .. C07C 309/06; C07C 381/12; C07D 307/64; C07D 333/46

USPC ....................... 560/138; 562/30, 42, 109, 113
See application file for complete search history.

(56) References Cited

U.S. PATENT DOCUMENTS

2010/0087563 A1 * 4/2010 Hayoz et al. .................... 522/25
2010/0113818 A1    5/2010 Oh et al.

FOREIGN PATENT DOCUMENTS

TW              201016649 A       5/2010

OTHER PUBLICATIONS

Taiwanese Office Action dated Jan. 6, 2014 in connection with the corresponding Taiwanese patent application.

* cited by examiner

*Primary Examiner* — Fereydoun G Sajjadi
*Assistant Examiner* — Amy C Bonaparte
(74) *Attorney, Agent, or Firm* — Davidson, Davidson & Kappel, LLC

(57) ABSTRACT

A sulfonium compound represented by the following formula (1), a photoacid generator containing the sulfonium compound, and a resist composition containing the photoacid generator are provided:

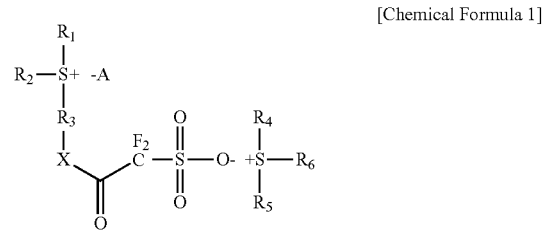

[Chemical Formula 1]

wherein X represents an electron donor group; $R_1$ and $R_2$ each independently represent an alkyl group or the like; $R_4$ to $R_6$ each independently represent an alkyl group, or the like; $R_3$ represents a cyclic alkenediyl group or the like; and –A represents an anion. The sulfonium compound has a photon yield that is controllable by introducing different absorbers to the cation region in one molecule, can address the inconvenience of using a mixture of different photoacid generators when the sulfonium compound is applied as a photoacid generator, has excellent miscibility in a resist, and has enhanced resolution and line edge roughness.

7 Claims, 3 Drawing Sheets

SULFONIUM COMPOUND, PHOTOACID GENERATOR, AND RESIST COMPOSITION

This application is a national phase application under a national phase application under priority under 35 U.S.C §119 from Korean Patent Application No. 10-2011-0077527, filed on Aug. 3, 2011, the disclosure of which is hereby incorporated by reference herein in its entirety.

BACKGROUND OF THE INVENTION

1. Field of the Invention

The present invention relates to a sulfonium compound, a photoacid generator, and a resist composition, and more particularly, to a sulfonium compound which has a photon yield that can be controlled by introducing absorbers that are different from each other to the cation region in one molecule, provides a compound having two acid sites respectively having an acid generator that is different from the other, thereby addressing the inconvenience of using a mixture of different photoacid generators, has excellent miscibility within a resist, and has improved miscibility with resists; a photoacid generator, and a resist composition.

2. Description of the Related Art

Semiconductor microprocessing technology utilizes lithographic processes, and in such lithographic processes, chemically amplified resist compositions are frequently used. Such a chemically amplified resist composition includes a photoacid generator which is a compound that generates acid when irradiated with light.

This photoacid generator generates acid when the photoacid generator absorbs light that is irradiated in the semiconductor patterning process.

In the case of an onium which is one of these photoacid generators, the onium is degraded to a cation form or a radical form when irradiated with light, and exists in a different molecular form, while an acid is generated at the anion side. Thus, diffusion of acid occurs on the resist film at the time of wafer baking after light irradiation.

A photoacid generator is capable of directly affecting the pattern characteristics of a resist, such as the resolution of the resist or the line edge roughness (LER), due to various characteristic factors such as an ability to absorb light, the acid generation efficiency, an ability to diffuse the generated acid, and the strength of acid of the anion.

Existing photoacid generators have a structure which can generate only one kind of acid per molecule, so that when a photoacid generator having characteristics such as both high diffusivity and low diffusivity and both high permeability and low permeability, is needed in order to obtain a high resolution, there is an inconvenience of using a mixture of photoacid generators. Furthermore, when photoacid generators are used in mixture, there is a problem that the photoacid generators cannot be uniformly mixed into the resist, and thereby a resist pattern having uniform characteristics may not be obtained.

As an example of the existing photoacid generator, Korean Patent Application No. 10-2006-00133676 (filed Jul. 2, 2007, by Sumitomo Chemical Co., Ltd.) discloses a compound represented by the following formula:

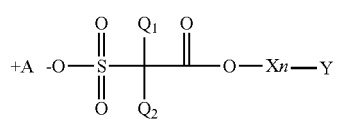

[Chemical Formula]

wherein in the above formula, X represents an alkylene group or a substituted alkylene group; Y represents a hydrocarbon group having 5 to 30 carbon atoms and containing one or more aromatic rings; $Q_1$ and $Q_2$ each independently represent a fluorine atom or a perfluoroalkyl group having 1 to 6 carbon atoms; A+ represents an organic counterion; and n represents 0 or 1.

In another instance, Korean Patent Application No. 10-2007-0062926 (filed Jun. 18, 2007, by Shin-Etsu Chemical Co., Ltd.) discloses a compound represented by the following formula:

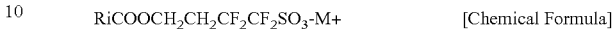

$RiCOOCH_2CH_2CF_2CF_2SO_3\text{-M+}$  [Chemical Formula]

wherein in the above formula, $R_1$ represents an alkyl group having 1 to 20 carbon atoms, an aryl group having 6 to 15 carbon atoms, or a heteroaryl group having 4 to 15 carbon atoms; and M+ represents a lithium ion, a sodium ion, a potassium ion, an ammonium ion or a tetramethylammonium ion.

It is described in the patent application filed by Shin-Etsu Chemical that a sulfonic acid represented by the above formula can exhibit strong acidity, various substituents can be introduced to the acid, and the range of molecular design flexibility is large.

However, the constitution of the existing acid generators is complicated because an acid generator having high diffusivity and an acid generator having low diffusivity, and an acid generator having high permeability and an acid generator having low permeability should be used together as a mixture in order to obtain high resolution. Also, in the case of using a mixture of two or more photoacid generators in order to obtain a photoacid generator having contradictory characteristics such as described above, there is a problem that uniform miscibility in the resist may not be obtained.

SUMMARY OF THE INVENTION

Accordingly, it is an object of the present invention to provide a sulfonium compound which has a photon yield that can be controlled, provides a compound having two acid sites respectively having an acid generator that is different from the other, thereby addressing the inconvenience of using a mixture of different photoacid generators, has excellent miscibility within a resist, and has improved miscibility with resists. It is another object of the present invention to provide an acid generator and a resist composition.

In order to achieve the objects described above, according to an aspect of the present invention, there is provided a sulfonium compound represented by the following formula (1):

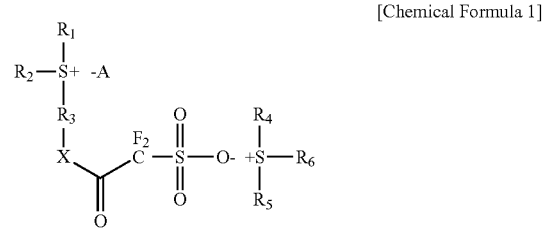

[Chemical Formula 1]

wherein in the formula (1), X represents an electron donor group; $R_1$ and $R_2$ each independently represent any one selected from the group consisting of an alkyl group, a cycloalkyl group, an aryl group, a heteroalkyl group, a heterocycloalkyl group and a heteroaryl group; $R_1$ and $R_2$ may be joined, together with the sulfur atom to which $R_1$ is bonded, to form a heterocycloalkyl group having 2 to 7 carbon atoms; $R_4$ to $R_6$ each independently represent any one selected from the group consisting of an alkyl group, a cycloalkyl group, an aryl group, a heteroalkyl group, a heterocycloalkyl group and a heteroaryl group; $R_4$ and $R_5$ may be joined, together with the sulfur atom to which $R_4$ is bonded, to form a heterocycloalkyl group having 2 to 7 carbon atoms; $R_3$ represents any one selected from the group consisting of a cyclic alkenediyl group, a heterocyclic alkenediyl group, an arylene group and a heteroarylene group; and –A represents an anion.

The anion –A may be any one selected from the group consisting of a sulfonate anion, an imide anion, a methide anion, a halogenated alkyl anion, a carboxylate anion, an iodonium anion and a sulfonylimide anion.

The anion –A may be any one selected from the group consisting of anions represented by the following formulas (1-1), (1-2) and (1-3):

[Chemical Formula 1-1]

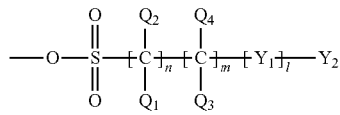

wherein in the formula (1-1), $Q_1$, $Q_2$, $Q_3$ and $Q_4$ each independently represent any one selected from the group consisting of a hydrogen atom, a halogen atom, and an alkyl group; $Y_1$ represents any one selected from the group consisting of an alkanediyl group, an alkenediyl group, NR', S, O, CO and combinations thereof; R' represents any one selected from the group consisting of a hydrogen atom and an alkyl group; $Y_2$ represents any one selected from the group consisting of a hydrogen atom, an alkyl group, a cycloalkyl group, a heterocycloalkyl group, an aryl group, a heteroaryl group, a heteroalkyl group, an allyl group, a perfluoroalkyl group, a haloalkyl group and an alkylsulfonyl group; n represents an integer from 0 to 10; m represents an integer from 0 to 10; and l represents an integer from 0 to 5;

[Chemical Formula 1-2]

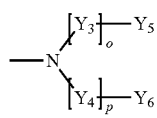

wherein in the formula (1-2), $Y_3$ and $Y_4$ each independently represent any one selected from the group consisting of alkanediyl, alkenediyl, NR', S, O, CO, $O_2S$ and combinations thereof; R' represents any one selected from the group consisting of a hydrogen atom and an alkyl group; $Y_5$ and $Y_6$ each independently represent any one selected from the group consisting of a hydrogen atom, an alkyl group, a cycloalkyl group, a heterocycloalkyl group, an aryl group, a heteroaryl group, a heteroalkyl group, an allyl group, a perfluoroalkyl group, a haloalkyl group and an alkylsulfonyl group; o represents an integer from 0 to 5; and p represents an integer from 0 to 5; and

[Chemical Formula 1-3]

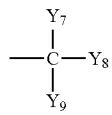

wherein in the formula (1-3), $Y_7$, $Y_8$ and $Y_9$ each independently represent any one selected from the group consisting of a hydrogen atom, an alkyl group, a cycloalkyl group, a heterocycloalkyl group, an aryl group, a heteroaryl group, a heteroalkyl group, an allyl group, a perfluoroalkyl group, a haloalkyl group and an alkylsulfonyl group.

The anion –A may be any one selected from the group consisting of $-OSO_2CF_3$, $-OSO_2C_4F_9$, $-OSO_2C_8F_{17}$, $-N(CF_3)_2$, $N(C_2F_5)_2$, $N(C_4F_9)_2$, $-C(CF_3)_3$, $-C(C_2F_5)_3$, $-C(C_4F_9)_3$, and an anion represented by the following formula (1-4):

[Chemical Formula 1-4]

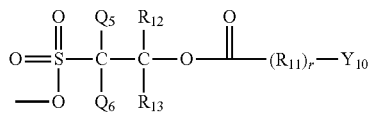

wherein in the formula (1-4), $Y_{10}$ represents any one selected from the group consisting of a cycloalkyl group, a heterocycloalkyl group, an aryl group, a heteroaryl group, an alkyl group, a heteroalkyl group, an allyl group, a perfluoroalkyl group, a haloalkyl group and an alkylsulfonyl group; $R_{11}$ represents any one selected from the group consisting of alkanediyl, alkenediyl, NR', S, O, CO and combinations thereof; R' represents any one selected from the group consisting of a hydrogen atom and alkyl group; $R_{12}$ and $R_{13}$ each independently represent any one selected from the group consisting of a hydrogen atom and an alkyl group having 1 to 8 carbon atoms; r represents an integer from 0 to 5; and $Q_5$ and $Q_6$ each independently represent a halogen atom.

The substituent $R_3$ may be any one selected from the group consisting of groups represented by the following formulas (2-1) to (2-4):

[Chemical Formula 2-1]

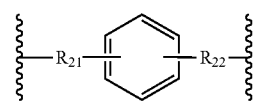

[Chemical Formula 2-2]

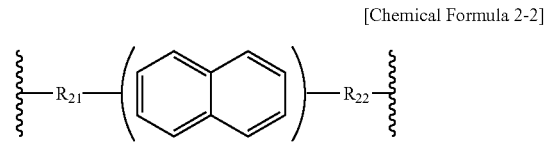

[Chemical Formula 2-3]

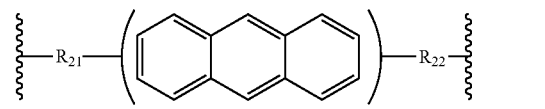

[Chemical Formula 2-4]

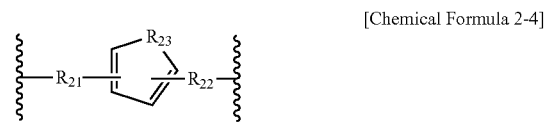

wherein in the formulas (2-1) to (2-4), $R_{21}$ and $R_{22}$ each independently represent any one selected from the group consisting of a single bond, an alkanediyl group having 1 to 5 carbon atoms, and an alkenediyl group having 2 to 5 carbon atoms; $R_{23}$ represents any one selected from the group consisting of $-CH_2-$, $-O-$ and $-S-$.

X may be any one selected from the group consisting of $-O-$, $-S-$, $-O-(CH_2)_n-O-$ (wherein n represents an integer from 1 to 5), —(CH$_2$)$_n$—S— (wherein n represents an integer from 1 to 5), and a group represented by the following formula (3-1):

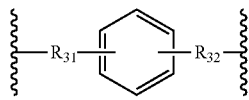

[Chemical Formula 3-1]

wherein in the formula (3-1), R$_{31}$ and R$_{32}$ each independently represent any one selected from the group consisting of —O—, —S—, and combinations thereof.

The sulfonium compound represented by the formula (1) may be any one selected from the group consisting of compounds represented by the following formula (5-1) to formula (5-3):

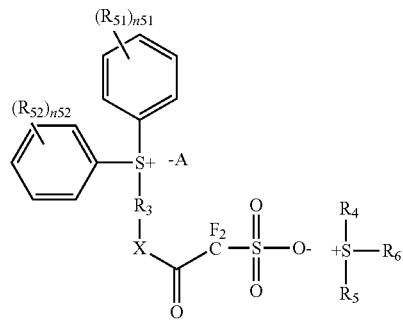

[Chemical Formula 5-1]

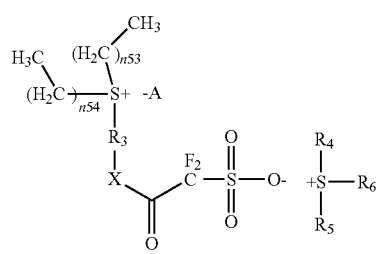

[Chemical Formula 5-2]

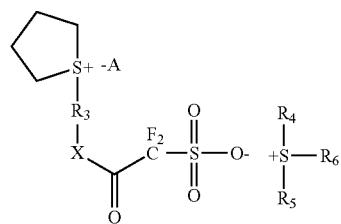

[Chemical Formula 5-3]

wherein in the formulas (5-1) to (5-3), R$_{51}$ and R$_{52}$ each independently represent any one selected from the group consisting of a hydrogen atom, an alkyl group having 1 to 5 carbon atoms, and a halogenated alkyl group having 1 to 5 carbon atoms; n51 and n52 each independently represent an integer from 1 to 5; n53 and n54 each independently represent an integer from 0 to 10; R$_3$ represents any one selected from the group consisting of a cycloalkenediyl group, a heterocycloalkenediyl group, an arylene group and a heteroarylene group; X represents an electron donor group; R$_4$ to R$_6$ each independently represent any one selected from the group consisting of an alkyl group, a cycloalkyl group, an aryl group, a heteroalkyl group, a heterocycloalkyl group, and a heteroaryl group; R$_4$ and R$_5$ may be joined, together with the sulfur atom to which R$_4$ is bonded, to form a heterocycloalkyl group having 2 to 7 carbon atoms; and -A represents an anion.

According to another aspect of the present invention, there is provided a photoacid generator containing the sulfonium compound described above.

According to another aspect of the present invention, there is provided a resist composition including the photoacid generator described above.

DESCRIPTION OF THE PREFERRED EMBODIMENTS

Figure 1:
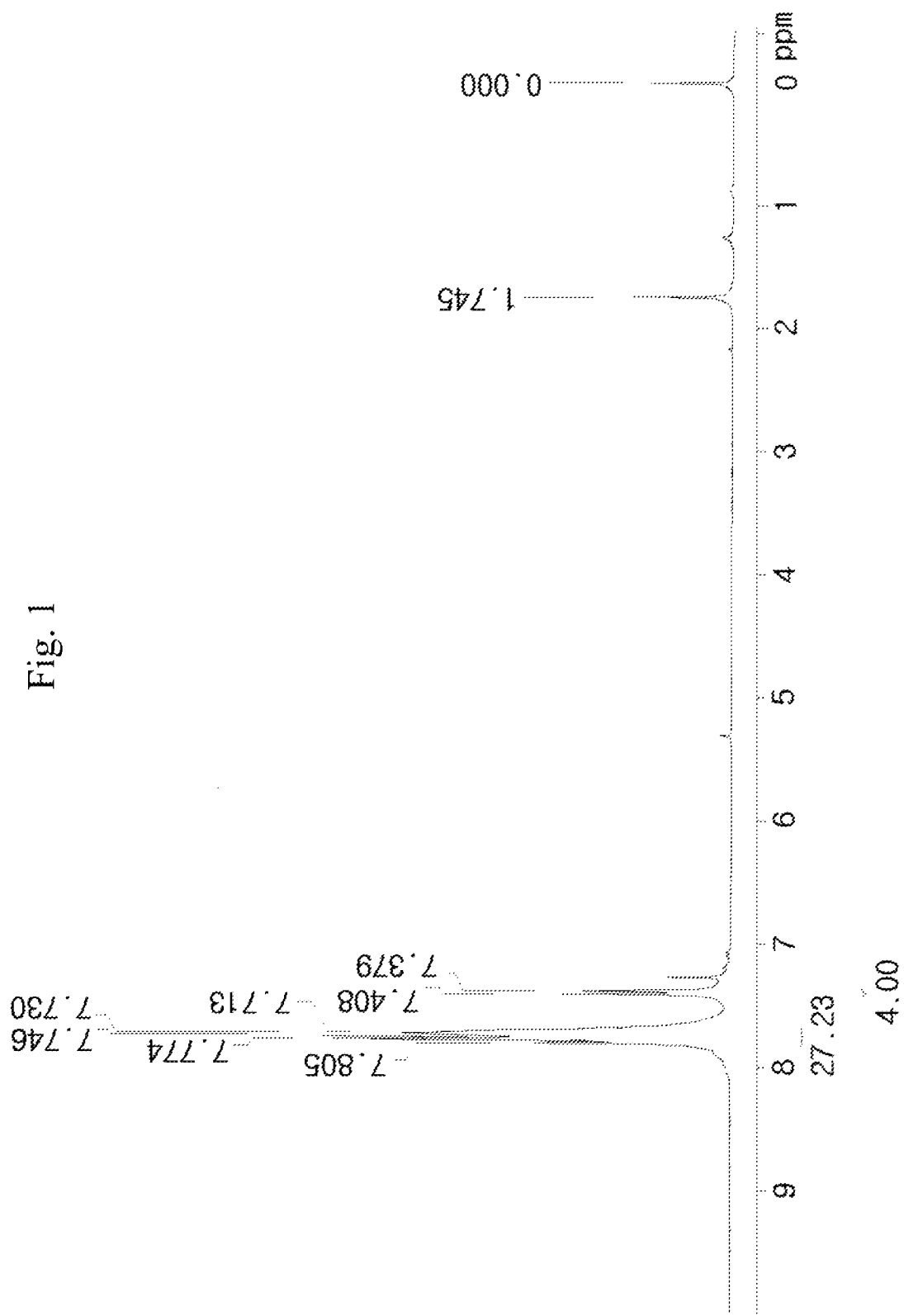
FIG. 1 is a graph showing the NMR data of compound [C] produced according to reaction scheme (1-5)

Hereinafter, the present invention will be described in more detail.

The terms used in the present specification are defined as follows.

Unless particularly stated otherwise in the specification, the halogen atom means any one selected from the group consisting of fluorine, chlorine, bromine and iodine.

Unless particularly stated otherwise in the specification, the alkyl group encompasses a linear alkyl group and a branched alkyl group, and encompasses a primary alkyl group, a secondary alkyl group and a tertiary alkyl group.

Unless particularly stated otherwise in the specification, the cycloalkyl group encompasses monocyclic, bicyclic, tricyclic and tetracyclic alkyl groups. The cycloalkyl group also encompasses polycyclic cycloalkyl groups, including an adamantyl group and a norbornyl group.

Unless particularly stated otherwise in the specification, the aryl group means a hydrocarbon containing one or two aromatic rings. Examples thereof include a benzyl group and a naphthyl group.

Unless particularly stated otherwise in the specification, the arylene group means a divalent atomic group obtained by excluding two hydrogen atoms from an arene, and the arene encompasses not only a hydrocarbon containing one benzene ring but also hydrocarbons containing 2 to 7 benzene rings, as well as derivatives thereof.

Unless particularly stated otherwise in the specification, the prefix "hetero-" means that one to three carbon atoms have been substituted by heteroatoms selected from the group consisting of —N—, —O—, —S— and —P—. For example, the heteroalkyl group means an alkyl group in which one to three carbon atoms have been substituted by heteroatoms.

Unless particularly stated otherwise in the specification, the prefix "halogenated" means that one hydrogen is substituted by any one atom selected from the group consisting of fluorine, chlorine, bromine and iodine.

Unless particularly stated otherwise in the specification, the alkanediyl group means a divalent atomic group obtained by excluding two hydrogen atoms from an alkane, and may be represented by the formula: —C$_n$H$_{2n}$—.

Unless particularly stated otherwise in the specification, the alkenediyl group means a divalent atomic group obtained by excluding two hydrogen atoms from an alkene, and may be represented by the formula: —$C_nH_{2n-2}$—.

Unless particularly stated otherwise in the specification, the cyclic alkenediyl group means a divalent atomic group obtained by excluding two hydrogen atoms from a cyclic alkene.

Unless particularly stated otherwise in the specification, the heterocyclic alkenediyl group means an atomic group in which one to three carbon atoms of a cycloalkenediyl have been substituted by one to three heteroatoms selected from the group consisting of —N—, —O—, —S— and —P—, and encompasses a furan, a thiophene and derivatives thereof.

Unless particularly stated otherwise in the specification, the haloalkyl group means a halogenated alkyl group.

Unless particularly stated otherwise in the specification, the alkylsulfonyl group means a compound containing an alkyl group and a sulfonyl group, or a derivative thereof.

Unless particularly stated otherwise in the specification, the perfluoroalkyl group means an alkyl group in which all or a part of the hydrogen atoms have been substituted by fluorine.

All the compounds and substituents used in the invention may be substituted or unsubstituted unless particularly stated otherwise. Here, the term "substituted" means that a hydrogen atom has been substituted by any one selected from the group consisting of a halogen atom, a hydroxyl group, a carboxyl group, a cyano group, a nitro group, an amino group, a thio group, a methylthio group, an alkoxy group, a nitrile group, an aldehyde group, an epoxy group, an ether group, an ester group, a carbonyl group, an acetal group, a ketone group, an alkyl group, a cycloalkyl group, a heterocycloalkyl group, an allyl group, a benzyl group, an aryl group, a heteroaryl group, a perfluoroalkyl group, derivatives thereof, and combinations thereof.

Unless particularly stated otherwise in the specification, the alkyl group means an alkyl group having 1 to 40 carbon atoms; the cycloalkyl group means a cycloalkyl group having 3 to 40 carbon atoms; the aryl group means an aryl group having 6 to 40 carbon atoms; the heteroalkyl group means a heteroalkyl group having 1 to 40 carbon atoms; the heterocycloalkyl group means a heterocycloalkyl group having 2 to 40 carbon atoms; the heteroaryl group means a heteroaryl group having 2 to 30 carbon atoms; the arylene group means an arylene group having 6 to 40 carbon atoms; the heteroarylene group means a heteroarylene group having 2 to 40 carbon atoms; the alkanediyl group means an alkanediyl group having 1 to 40 carbon atoms; the alkenediyl group means an alkenediyl group having 2 to 40 carbon atoms; the allyl group means an allyl group having 3 to 40 carbon atoms; the perfluoroalkyl group means a perfluoroalkyl group having 1 to 30 carbon atoms; the haloalkyl group means a haloalkyl group having 1 to 30 carbon atoms; and the alkylsulfonyl group means an alkylsulfonyl group having 1 to 30 carbon atoms.

The sulfonium compound according to an embodiment of the present invention is represented by the following formula (1):

[Chemical Formula 1]

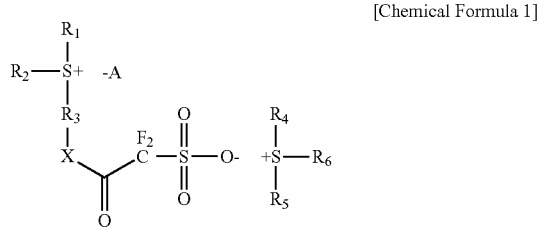

wherein in the formula (1), $R_1$ and $R_2$ each independently represent any one selected from the group consisting of an alkyl group, a cycloalkyl group, an aryl group, a heteroalkyl group, a heterocycloalkyl group and a heteroaryl group, or $R_1$ and $R_2$ may be joined, together with the sulfur atom to which $R_1$ is bonded, to form a heterocycloalkyl group having 2 to 7 carbon atoms.

In the formula (1), $R_4$ to $R_6$ each independently represent any one selected from the group consisting of an alkyl group, a cycloalkyl group, an aryl group, a heteroalkyl group, a heterocycloalkyl group and a heteroaryl group, or $R_4$ and $R_5$ may be joined, together with the sulfur atom to which $R_4$ is bonded, to form a heterocycloalkyl group having 2 to 7 carbon atoms.

$R_4$ to $R_6$ each independently represent any one selected from the group consisting of an alkyl group having 1 to 20 carbon atoms, a cycloalkyl group having 3 to 20 carbon atoms, an aryl group having 6 to 20 carbon atoms, a heteroalkyl group having 4 to 20 carbon atoms, a heterocycloalkyl group having 3 to 25 carbon atoms, and a heteroaryl group having 6 to 20 carbon atoms, or $R_4$ and $R_5$ may be joined, together with the sulfur atom to which $R_4$ is bonded, to form a heterocycloalkyl group having 3 to 6 carbon atoms.

In the formula (1), $R_3$ represents any one selected from the group consisting of a cyclic alkenediyl group, a heterocyclic alkenediyl group, an arylene group and a heteroarylene group, and X represents an electron donor group.

$R_3$ represents any one selected from the group consisting of a cyclic alkenediyl group having 3 to 15 carbon atoms, a heterocyclic alkenediyl group having 3 to 15 carbon atoms, an arylene group having 6 to 25 carbon atoms, and a heteroarylene group having 5 to 20 carbon atoms, and the arylene group and the heteroarylene group may each independently have one to four benzene rings, and the heterocyclic alkenediyl group may be derived from a furan or a thiophene.

$R_3$ may be any one selected from the group consisting of groups represented by the following formulas (2-1) to (2-4):

[Chemical Formula 2-1]

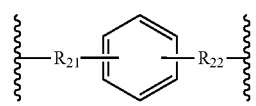

[Chemical Formula 2-2]

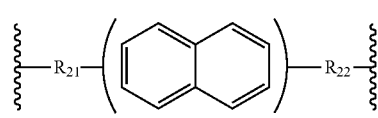

[Chemical Formula 2-3]

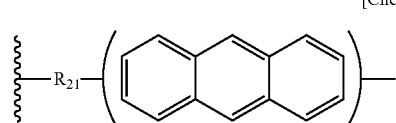

[Chemical Formula 2-4]

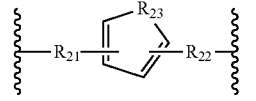

wherein in the formulas (2-1) to (2-4), $R_{21}$ and $R_{22}$ each independently represent any one selected from the group consisting of a single bond, an alkanediyl group having 1 to 5 carbon atoms, and an alkenediyl group having 2 to 5 carbon atoms; and $R_{23}$ represents any one selected from the group consisting of —$CH_2$—, —O— and —S—.

X may be any one selected from the group consisting of —O—, —S—, —O—(CH$_2$)$_n$—O— (wherein n represents an integer from 1 to 5), —(CH$_2$)$_n$—S— (wherein n represents an integer from 1 to 5), and a group represented by the following formula (3-1):

[Chemical Formula 3-1]

$$\text{—R}_{31}\text{—}\underset{}{\underset{}{\bigcirc}}\text{—R}_{32}\text{—}$$

wherein in the formula (3-1), R$_{31}$ and R$_{32}$ each independently represent any one selected from the group consisting of —O—, —S— and combinations thereof.

The group —R$_3$—X— may be any one selected from the group consisting of groups represented by the following formulas (4-1) to (4-4):

[Chemical Formula 4-1]

[Chemical Formula 4-2]

[Chemical Formula 4-3]

[Chemical Formula 4-4]

wherein in the formulas (4-1) to (4-4), R$_{41}$ represents any one selected from the group consisting of —O—, —S— and —O—(CH$_2$)$_n$—O— (wherein n represents an integer from 1 to 5); R$_{42}$ represents any one selected from the group consisting of —(CH$_2$)$_n$—S— (wherein n represents an integer from 1 to 5) and —(CH$_2$)$_n$—O— (wherein n represents an integer from 1 to 5); and R$_{43}$ represents any one selected from the group consisting of —CH$_2$—, —O— and —S—.

In the formula (1), -A represents an anion.

The anion -A may be any one selected from the group consisting of a sulfonate anion, an imide anion, a methide anion, a halogenated alkyl anion, a carboxylate anion, an iodonium anion, and a sulfonylimide anion.

The anion -A may be any one selected from the group consisting of anions represented by the following formulas (1-1), (1-2) and (1-3):

[Chemical Formula 1-1]

$$\text{-O}-\underset{\underset{O}{\|}}{\overset{\overset{O}{\|}}{S}}-(\underset{Q_1}{\overset{Q_2}{\underset{|}{C}}})_n-(\underset{Q_3}{\overset{Q_4}{\underset{|}{C}}})_m-(Y_1)_l-Y_2$$

wherein in the formula (1-1), Q$_1$, Q$_2$, Q$_3$ and Q$_4$ each independently represent any one selected from the group consisting of a hydrogen atom, a halogen atom, and an alkyl group; and may be each independently any one selected from the group consisting of a hydrogen atom, a halogen atom, and an alkyl group having 1 to 5 carbon atoms.

In the formula (1-1), Y$_1$ represents any one selected from the group consisting of an alkanediyl, an alkenediyl, NR', S, O, CO and combinations thereof, and R' represents any one selected from the group consisting of a hydrogen atom and an alkyl group. Furthermore, Y$_1$ may be any one selected from the group consisting of an alkanediyl having 2 to 20 carbon atoms, an alkenediyl having 2 to 20 carbon atoms, NR', S, O, CO and combinations thereof (wherein R' represents any one selected from the group consisting of a hydrogen atom and an alkyl group having 1 to 5 carbon atoms).

In the formula (1-1), Y$_2$ represents any one selected from the group consisting of a hydrogen atom, an alkyl group, a cycloalkyl group, a heterocycloalkyl group, an aryl group, a heteroaryl group, a heteroalkyl group, an allyl group, a perfluoroalkyl group, a haloalkyl group and an alkylsulfonyl group, and Y$_2$ may be any one selected from the group consisting of a hydrogen atom, an alkyl group having 1 to 10 carbon atoms, a cycloalkyl group having 3 to 20 carbon atoms, a heterocycloalkyl group having 3 to 20 carbon atoms, an aryl group having 6 to 20 carbon atoms, a heteroaryl group having 5 to 20 carbon atoms, a heteroalkyl group having 1 to 10 carbon atoms, an allyl group having 2 to 15 carbon atoms, a perfluoroalkyl group having 1 to 8 carbon atoms, a haloalkyl group having 1 to 10 carbon atoms, and an alkylsulfonyl group having 1 to 15 carbon atoms.

In the formula (1-1), n represents an integer from 0 to 10, and may be an integer from 0 to 5. m represents an integer from 0 to 10, and may be an integer from 0 to 5.

In the formula (1-1), l represents an integer from 0 to 5, and may be an integer from 0 to 2.

[Chemical Formula 1-2]

$$-\text{N}\underset{\underset{[Y_4]_p-Y_6}{}}{\overset{[Y_3]_o-Y_5}{\diagup}}$$

wherein in the formula (1-2), Y$_3$ and Y$_4$ each independently represent any one selected from the group consisting of an alkanediyl, an alkenediyl, NR', S, O, CO, O$_2$S and combinations thereof (wherein R' represents any one selected from the group consisting of a hydrogen atom and an alkyl group), and Y$_3$ and Y$_4$ may be each independently any one selected from the group consisting of an alkanediyl having 2 to 15 carbon atoms, an alkenediyl having 2 to 15 carbon atoms, NR', S, O, CO, O$_2$S and combinations thereof (R' represents any one selected from the group consisting of a hydrogen atom and an alkyl group).

In the formula (1-2), Y$_5$ and Y$_6$ each independently represent any one selected from the group consisting of a hydrogen atom, an alkyl group, a cycloalkyl group, a heterocycloalkyl group, an aryl group, a heteroaryl group, a heteroalkyl group, an allyl group, a perfluoroalkyl group, a haloalkyl group, and an alkylsulfonyl group, and Y$_5$ and Y$_6$ may be each independently any one selected from the group consisting of an alkyl group having 1 to 10 carbon atoms, a cycloalkyl group having 3 to 20 carbon atoms, a heterocycloalkyl group having 3 to 20 carbon atoms, an aryl group having 6 to 20 carbon atoms, a heteroaryl group having 5 to 20 carbon atoms, a heteroalkyl group having 1 to 10 carbon atoms, an allyl group having 2 to 15 carbon atoms, a perfluoroalkyl group having 1 to 8 carbon atoms, a haloalkyl group having 1 to 10 carbon atoms, and an alkylsulfonyl group having 1 to 15 carbon atoms.

In the formula (1-2), o represents an integer from 0 to 5, and p represents an integer from 0 to 5.

[Chemical Formula 1-3]

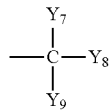

wherein in the formula (1-3), $Y_7$, $Y_8$ and $Y_9$ each independently represent any one selected from the group consisting of a hydrogen atom, an alkyl group, a cycloalkyl group, a heterocycloalkyl group, an aryl group, a heteroaryl group, a heteroalkyl group, an allyl group, a perfluoroalkyl group, a haloalkyl group and an alkylsulfonyl group, and $Y_7$, $Y_8$ and $Y_9$ may be each independently any one selected from the group consisting of a hydrogen atom, an alkyl group having 1 to 10 carbon atoms, a cycloalkyl group having 3 to 20 carbon atoms, a heterocycloalkyl group having 3 to 20 carbon atoms, an aryl group having 6 to 20 carbon atoms, a heteroaryl group having 5 to 20 carbon atoms, a heteroalkyl group having 1 to 10 carbon atoms, an allyl group having 2 to 15 carbon atoms, a perfluoroalkyl group having 1 to 8 carbon atoms, a haloalkyl group having 1 to 10 carbon atoms, and an alkylsulfonyl group having 1 to 15 carbon atoms.

The anion –A may be any one selected from the group consisting of $-OSO_2CF_3$, $-OSO_2C_4F_9$, $-OSO_2C_8F_{17}$, $-N(CF_3)_2$, $N(C_2F_5)_2$, $N(C_4F_9)_2$, $-C(CF_3)_3$, $-C(C_2F_5)_3$, $-C(C_4F_9)_3$, and an anion represented by the following formula (1-4):

[Chemical Formula 1-4]

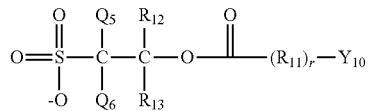

wherein in the formula (1-4), $Y_{10}$ represents any one selected from the group consisting of a cycloalkyl group, a heterocycloalkyl group, an aryl group, a heteroaryl group, an alkyl group, a heteroalkyl group, an allyl group, a perfluoroalkyl group, a haloalkyl group, and an alkylsulfonyl group, and may be any one selected from the group consisting of a cycloalkyl group having 3 to 20 carbon atoms, a heterocycloalkyl group having 2 to 20 carbon atoms, an aryl group having 6 to 25 carbon atoms, a heteroaryl group having 6 to 20 carbon atoms, an alkyl group having 1 to 20 carbon atoms, a heteroalkyl group having 1 to 20 carbon atoms, an allyl group having 2 to 20 carbon atoms, a perfluoroalkyl group having 1 to 10 carbon atoms, a haloalkyl group having 1 to 10 carbon atoms, and an alkylsulfonyl group having 1 to 10 carbon atoms.

In the formula (1-4), $R_{11}$ represents any one selected from the group consisting of an alkanediyl, and alkenediyl, NR', S, O, CO and combinations thereof (wherein R' represents any one selected from the group consisting of a hydrogen atom and an alkyl group), and $R_{11}$ may be any one selected from the group consisting of an alkanediyl having 2 to 20 carbon atoms, an alkenediyl having 2 to 20 carbon atoms, NR', S, O, CO and combinations thereof (wherein R' represents any one selected from the group consisting of a hydrogen atom and an alkyl group having 1 to 5 carbon atoms).

In the formula (1-4), $R_{12}$ and $R_{13}$ each independently represent any one selected from the group consisting of a hydrogen atom and an alkyl group having 1 to 8 carbon atoms.

In the formula (1-4), r represents an integer from 0 to 5, and r may be an integer from 0 to 3.

In the formula (1-4), $Q_5$ and $Q_6$ each independently represent a halogen atom, and each may be a fluorine atom.

Furthermore, –A may be any one selected from the group consisting of $-OSO_2CF_3$, $-OSO_2CF_2CF_2CF_3$, $-OSO_2CF_2CF_2CF_2CF_3$ and anions represented by the following formulas (1-5) to (1-8):

[Chemical Formula 1-5]

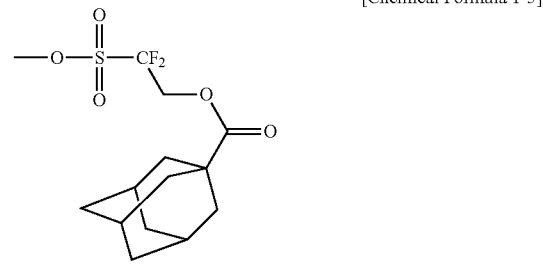

[Chemical Formula 1-6]

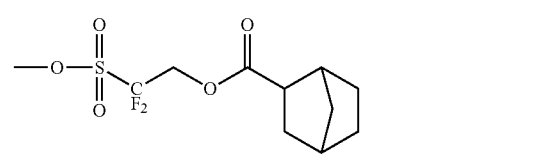

[Chemical Formula 1-7]

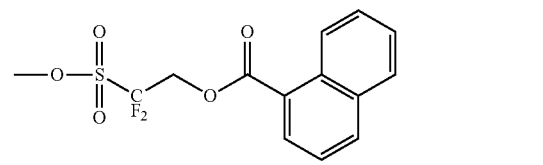

[Chemical Formula 1-8]

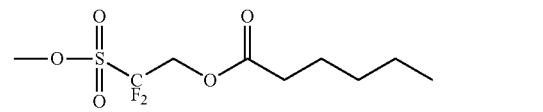

The sulfonium compound represented by the formula (1) has a structure having absorbers that are different from each other introduced into the cation region in one molecule, and can provide a photoacid generator which has a controllable photon yield, provides a compound having two acid sites respectively having a photoacid generator that is different from the other when applied as a photoacid generator, thereby addressing the inconvenience of using a mixture of different photoacid generators, and has excellent miscibility within a resist.

The sulfonium compound represented by the formula (1) may be preferably any one selected from the group consisting of compounds represented by the following formula (5-1) to formula (5-3):

[Chemical Formula 5-1]

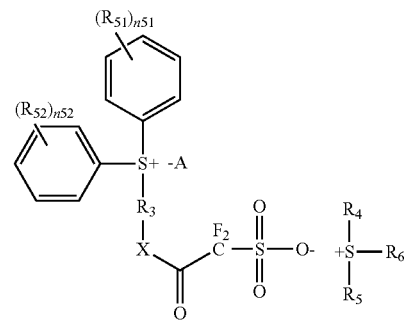

[Chemical Formula 5-2]

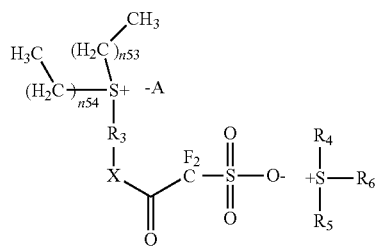

[Chemical Formula 5-3]

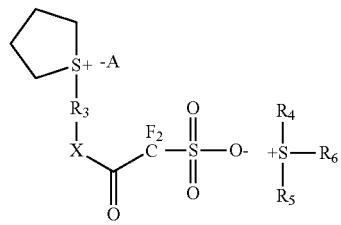

wherein in the formulas (5-1) to (5-3), $R_{51}$ and $R_{52}$ each independently represent any one selected from the group consisting of a hydrogen atom, an alkyl group having 1 to 5 carbon atoms, and a halogenated alkyl group having 1 to 5 carbon atoms; and may be any one selected from the group consisting of a hydrogen atom, an alkyl group having 1 to 3 carbon atoms, and a halogenated alkyl group having 1 to 3 carbon atoms.

In the formulas (5-1) to (5-3), n51 and n52 each independently represent an integer from 1 to 5, and may be each independently an integer from 1 to 3.

In the formulas (5-1) to (5-3), n53 and n54 each independently represent an integer from 0 to 10, and may be each independently an integer from 0 to 5.

In the formulas (5-1) to (5-3), $R_4$ to $R_6$ respectively have the same meanings as defined in relation to the formula (1), and therefore, further descriptions thereon will not be repeated. Also, $R_3$, X and –A respectively have the same meanings as defined in relation to the formula (1), and therefore, further descriptions thereon will not be repeated.

The sulfonium compound represented by the formula (1) may be any one selected from the group consisting of compounds represented by the following formula (6-1) to (6-22):

[Chemical Formula 6-1]

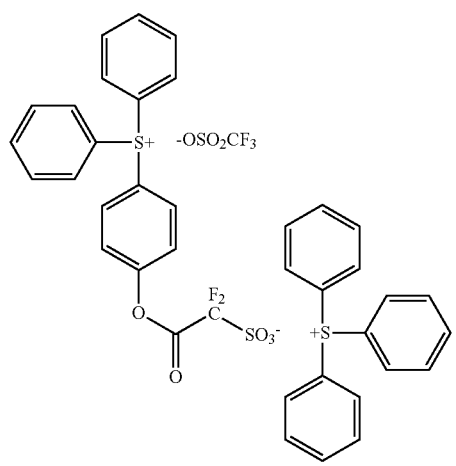

[Chemical Formula 6-2]

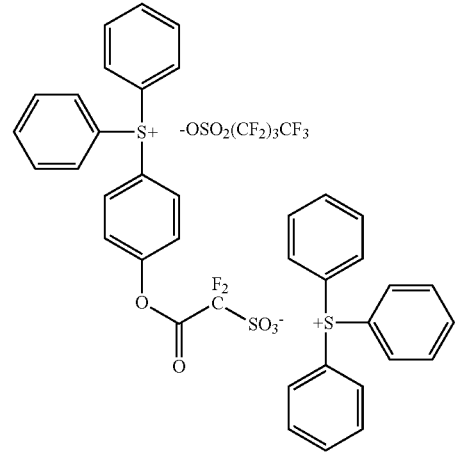

[Chemical Formula 6-3]

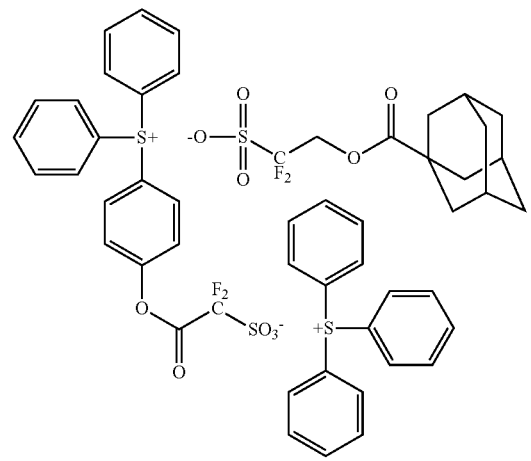

[Chemical Formula 6-4]

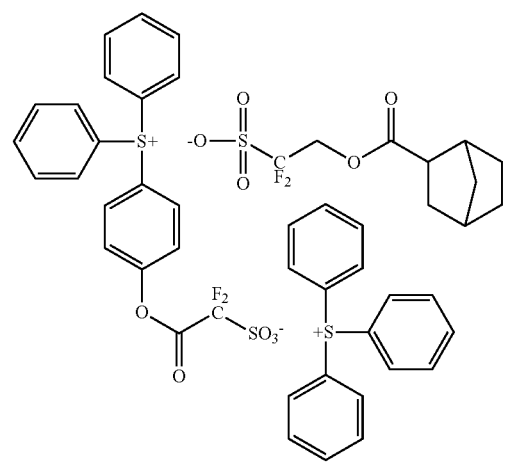

[Chemical Formula 6-5]
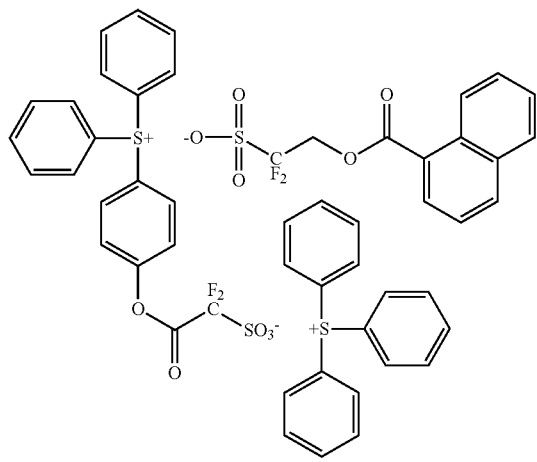
[Chemical Formula 6-8]
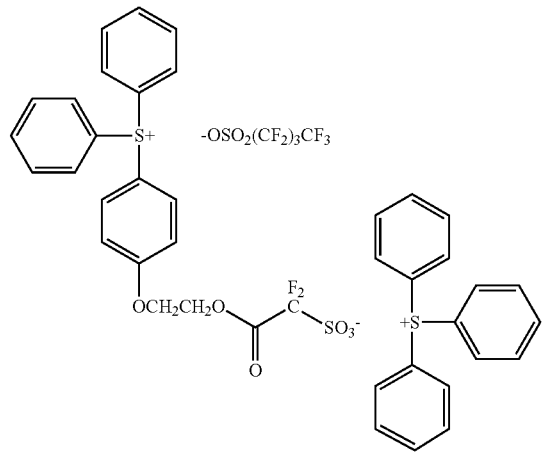
[Chemical Formula 6-6]
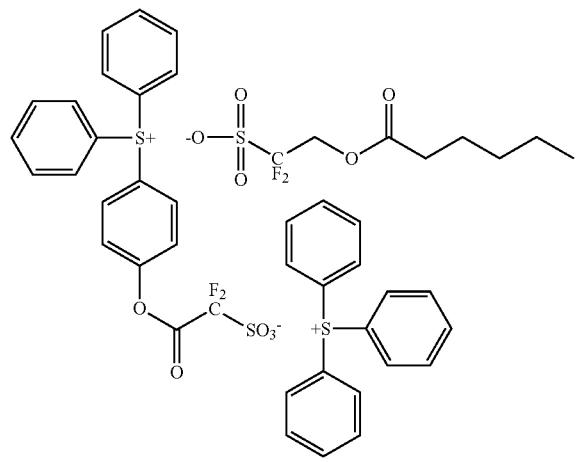
[Chemical Formula 6-9]
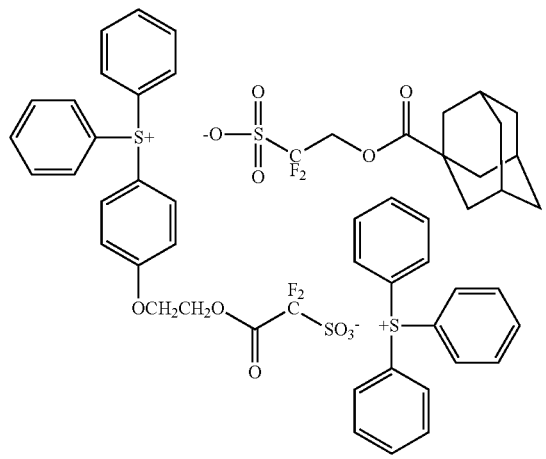
[Chemical Formula 6-7]
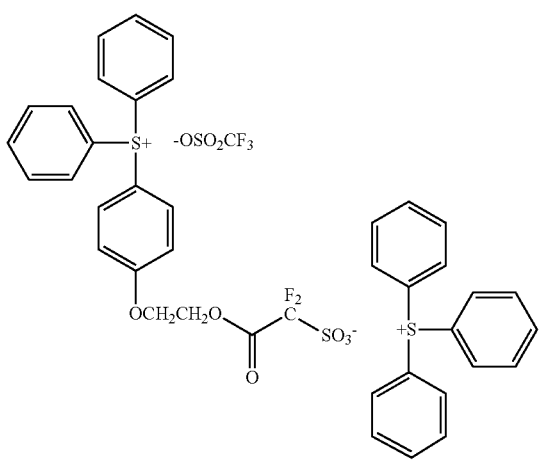
[Chemical Formula 6-10]
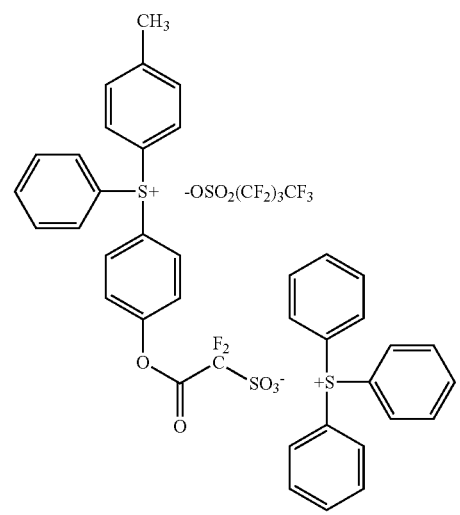

[Chemical Formula 6-11]
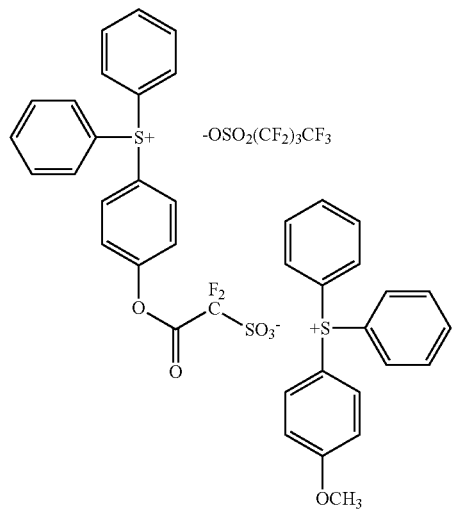
[Chemical Formula 6-12]
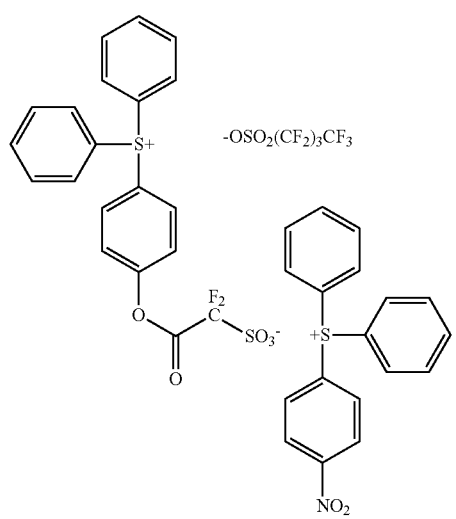
[Chemical Formula 6-13]
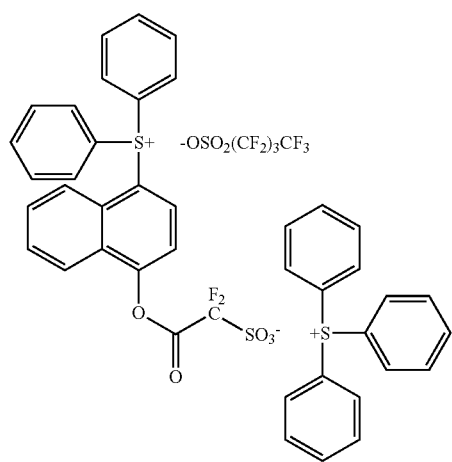
[Chemical Formula 6-14]
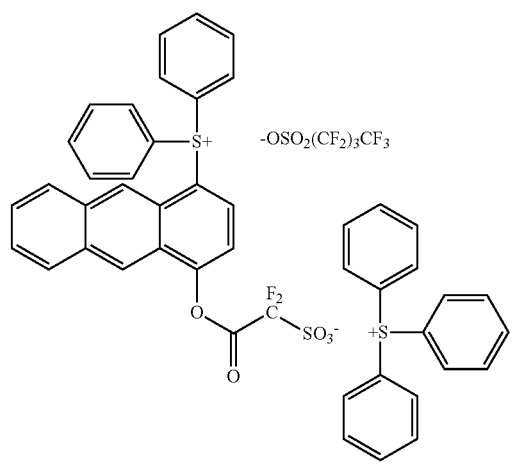
[Chemical Formula 6-15]
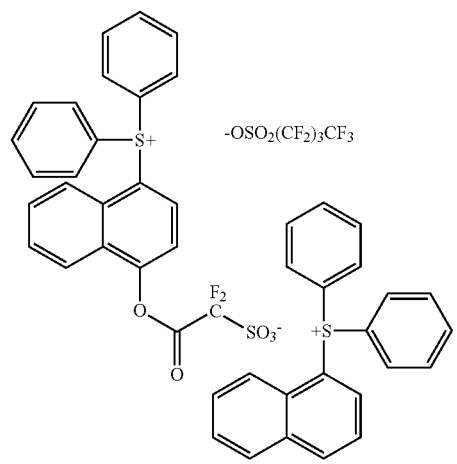
[Chemical Formula 6-16]
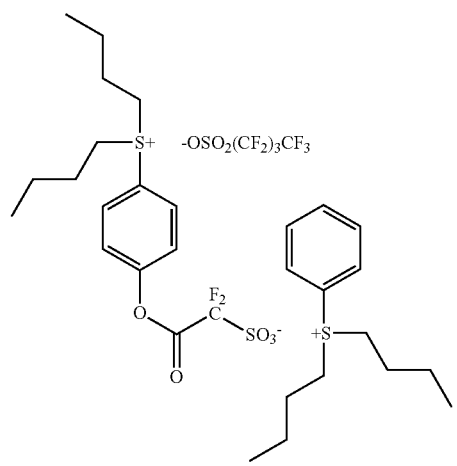

[Chemical Formula 6-17]

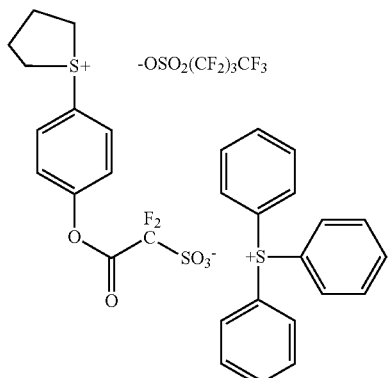

[Chemical Formula 6-18]

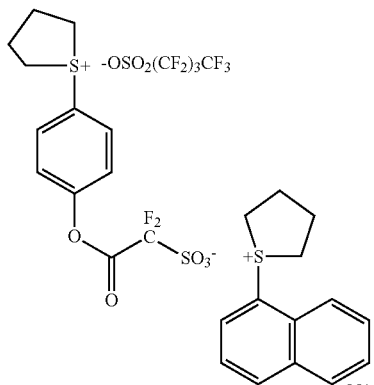

[Chemical Formula 6-19]

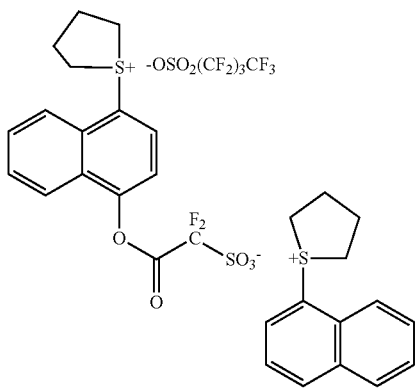

[Chemical Formula 6-20]

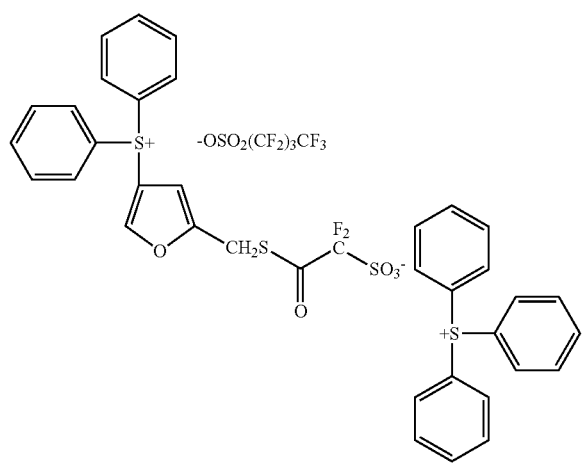

[Chemical Formula 6-21]

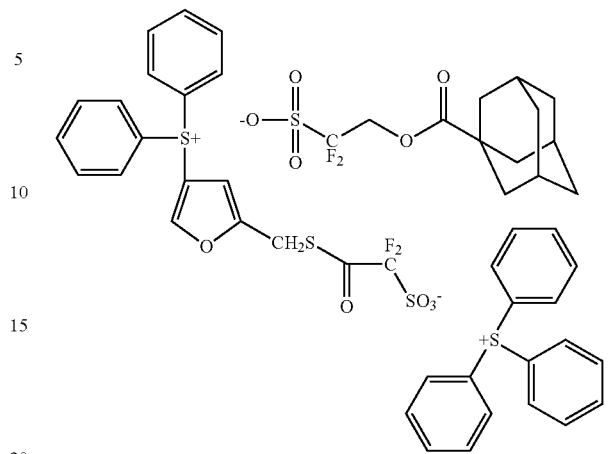

[Chemical Formula 22]

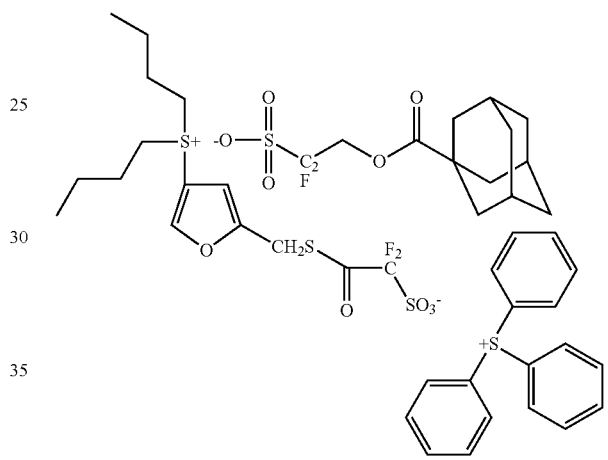

The sulfonium compounds represented by the above formulas can generate two acids having different diffusivities when generated at the time of light irradiation when the sulfonium compounds are applied as photoacid generators, and thereby can address problems such as non-uniform diffusion occurring in the case of mixing photoacid generators that are different from each other. The sulfonium compounds can also increase the resolution, and can improve the line edge roughness.

The photoacid generator according to another embodiment of the present invention contains the sulfonium compound represented by the formula (1). The descriptions on the sulfonium compound represented by the formula (1) are the same as the descriptions on the sulfonium compound described above, and therefore, further description will not be repeated.

When the sulfonium compound is applied as a photoacid generator, although a mixture of different photoacid generators having different characteristics such as high diffusivity and low diffusivity, or high permeability and low permeability, is not used, high resolution can be obtained, and excellent miscibility within a resist can be obtained.

The resist composition according to another embodiment of the present invention includes the photoacid generator described above. The resist composition can be constructed by incorporating together with the photoacid generator described above, any one selected from the group consisting of a copolymer, a solvent, an additive and combinations thereof.

The copolymer is not particularly limited as long as it is included in the resist composition and can form a resist film. Any solvent can be used as long as it is an organic solvent that is conventionally applied in resist compositions, and specific examples include lactones, amides, aromatic hydrocarbons, ketones, esters (including aliphatic carboxylic acid esters, lactic acid esters, and propylene glycol monoalkyl ether acetates), propylene glycol dialkyl ethers, propylene glycol monoalkyl ethers, and ethylene glycol monoalkyl ether acetates.

The additive may be any additive that is conventionally applied to resist compositions, and specifically, the additive may be any one selected from the group consisting of an alkali dissolution inhibitor, an acid diffusion inhibitor, a surfactant, a sensitizer and combinations thereof.

The alkali dissolution inhibitor may be any alkali dissolution inhibitor that is conventionally applied to resist compositions, and may be a phenol or carboxylic acid derivative.

The acid diffusion inhibitor may has an operation of controlling the phenomenon of diffusion of the acid generated by light irradiation in the resist coating film, and thereby suppresses the chemical reaction at an unexposed area. Amines including monoalkylamines such as n-hexylamine; and nitrogen compounds including diethylenediamine can be applied, but are not limited to these.

The surfactant is intended to improve coatability, developability and the like, and examples thereof include polyoxyethylene lauryl ether, polyoxyethylene stearyl ether, and polyoxyethylene, polyethylene glycol dilaurate, but are not limited to these.

Examples of the sensitizer include benzobazoles, anthracenes, and carbazoles, but are not limited to these.

The resist composition may include the photoacid generator in an amount of 0.001 to 99 parts by weight, preferably 0.1 to 20 parts by weight, and more preferably 1 to 11 parts by weight, relative to 100 parts by weight of the copolymer.

When the resist composition includes the photoacid generator in the content range described above, the resolution and the line edge roughness (LER) can be enhanced.

A resist composition including the photoacid generator has excellent miscibility, and can obtain the effect of high resolution that is obtainable by using a mixture of photoacid generators having high diffusivity and low diffusivity, and high permeability and low permeability, even without using a mixture of photoacid generators having different characteristics.

The sulfonium compound of the present invention has a photon yield that is controllable by introducing two different absorbers to the cation region in one molecule, can address the inconvenience of using a mixture of photoacid generators that are different from each other when the sulfonium compound is applied as a photoacid generator, has excellent miscibility within a resist, and can enhance the resolution and line edge roughness.

EXAMPLES

Here, the present invention will be described in detail by way of Examples so that those having ordinary skill in the art to which the present invention is pertained can easily carry out the invention. However, the present invention can be realized in various different forms, and are not intended to be limited to the Examples described herein.

Synthesis Example of Sulfonium Compound

Synthesis Example 1

1) 100 g of phenyl acetate represented [A] in the following reaction scheme (1-1) and 133.1 g of phenyl sulfoxide represented by [B] in the following reaction scheme (1-1) were mixed in 1200 ml of dichloromethane (MC) under stirring, and thus a mixed solution was prepared. The reaction temperature of the mixed solution was lowered to −78° C. using dry ice and acetone.

204 g of trifluoromethanesulfonic anhydride ($CF_3SO_2$)$_2$O) was placed in a dropping funnel at −78° C. and was slowly added dropwise to the mixed solution prepared above.

The dropwise addition was carried out for 3 hours at the reaction temperature, and the resulting mixture was stirred. Subsequently, when the starting materials disappeared on thin layer chromatography (TLC), the reaction was completed. Thus, a reaction solution was prepared.

To a solution prepared by dissolving 200 g of calcium carbonate in 1.5 L of water and cooled to 0° C., the reaction solution was added, and the mixture was vigorously stirred. The organic layer was removed 20 minutes after the stirring (first stirring) and was mixed with a solution having the same composition as the solution prepared by mixing calcium carbonate and water. The mixture was stirred again (second stirring), and the organic layer was extracted to obtain a reaction liquid.

The reaction liquid was washed with brine, and was dried over magnesium sulfate. The reaction liquid was filtered and concentrated, and thus 200 g (yield: 58.5%) of (4-acetoxyphenyl)diphenylsulfonium trifluoromethanesulfonate represented by [C] in the following reaction scheme (1-1) was obtained.

The structure of the compound represented by [C] in the following reaction scheme (1-1) was confirmed by $^1$H-NMR.

$^1$H-NMR (CDCl$_3$, internal standard: tetramethylsilane): δ (ppm) 5.34 (s, 2H), 7.38 (d, 2H), 7.77-7.84 (m, 2H)

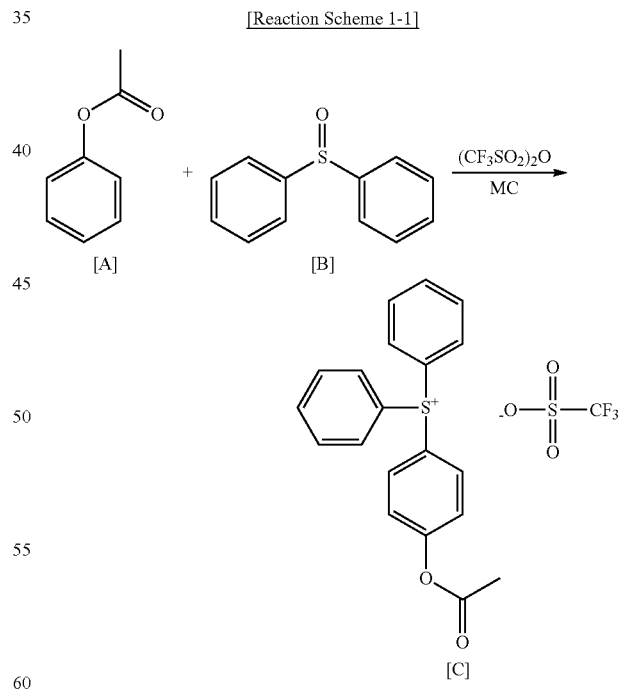

[Reaction Scheme 1-1]

2) 100 g of (4-acetoxyphenyl)diphenylsulfonium trifluoromethanesulfonate represented by [A] in the following reaction scheme (1-2), which had been produced in section (1) of Synthesis Example 1, was mixed with 300 ml of dichloromethane (MC) and 200 ml of distilled water under stirring, and thus a mixed solution was prepared.

10 g of p-toluenesulfonic acid represented by [B] in the following reaction scheme (1-2) was added dropwise to the mixed solution, and the resulting mixture was heated and stirred at 40° C. When the starting materials disappeared on thin layer chromatography (TLC), the reaction was completed, and thus a reaction solution was prepared.

Dichloromethane was added to the reaction solution, and then the mixture was subjected to layer separation. The organic layer was removed, washed two times with brine, and dried over magnesium sulfate. Thus, a reaction liquid was prepared.

The reaction liquid was filtered and concentrated, and thus 100 g (yield: 71%) of diphenyl-4-hydroxyphenylsulfonium trifluoromethanesulfonate represented by [C] in the following reaction scheme (1-2) was obtained.

The structure of the compound represented by [C] in the following reaction scheme (1-2) was confirmed by $^1$H-NMR.

$^1$H-NMR (CDCl$_3$, internal standard: tetramethylsilane): δ (ppm) 7.12 (d, 2H), 7.69-7.83 (m, 12H), 11.12 (br, 1H)

[Reaction Scheme 1-2]

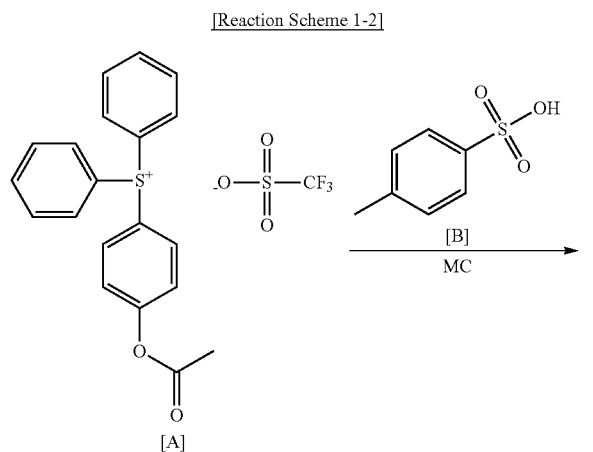

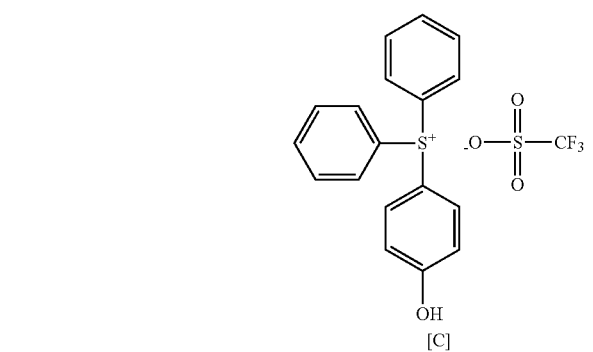

3) 100 g of difluorosulfoacetic acid sodium salt represented by [A] in the following reaction scheme (1-3) was mixed with 120 g of thionyl chloride (SOCl$_2$), and the mixture was heated and stirred for 3 hours at 80° C. The completion point of the reaction was confirmed by $^{19}$F-NMR, and the reaction solution was concentrated. The crude reaction solution was washed with ether, and thus 87 g of chlorocarbonyldifluoromethanesulfonic acid sodium salt represented by [B] in the following reaction scheme (1-3) was obtained (white solid, yield: 80%).

[Reaction Scheme 1-3]

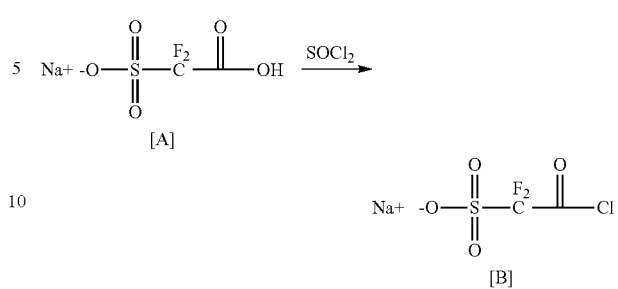

4) 50 g of the compound [A] and 25.3 g of the compound [B] of the following reaction scheme (1-4) were dissolved in 500 ml of 1,2-dichloroethane (DCE), and 20 g of diisopropylethylamine (DIPEA) was slowly added to the solution. The mixture was stirred, and thus a mixed solution was prepared.

After completion of the dropwise addition, the mixed solution was heated and stirred for 3 hours at 50° C. and was allowed to react. Thus, a reaction solution was prepared. The completion point of the reaction was confirmed by TLC, and when the reaction was completed, the reaction solution was washed with an aqueous HCl solution and distilled water in this order, and the organic layer was concentrated. The concentrated organic layer (crude reaction liquid) was purified using ether, and a compound represented by [C] in the following reaction scheme (1-4) was obtained (46.3 g, yield 65%).

[Reaction scheme 1-4]

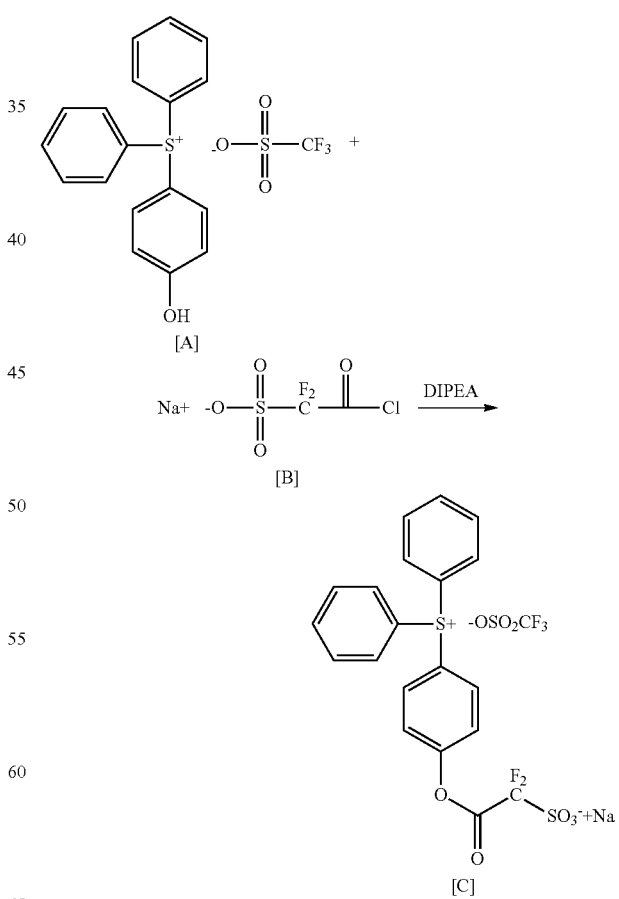

5) A mixed solution prepared by dissolving 50 g of the compound represented by [A] in the following reaction scheme (1-5) and 27 g of triphenylsulfonium trifluoromethanesulfonate represented by [B] in the following formula (1-5) in 200 ml of dichloromethane (MC) and 200 ml of distilled water was vigorously stirred for 5 hours at room temperature (about 25° C.), and thus a reaction solution was prepared. The completion point of the reaction of the reaction solution was confirmed by $^{19}$F-NMR, and after completion of the reaction, the reaction solution was washed with an aqueous solution of $K_2CO_3$ and distilled water. The organic layer was concentrated, and thus a reaction liquid was prepared. The crude reaction liquid was purified using dichloromethane and hexane, and thus 50.2 g (yield 90%) of a compound represented by [C] in the following reaction scheme (1-5) was obtained.

FIG. 1 presents the NMR data of the compound [C] produced by the reaction scheme (1-5).

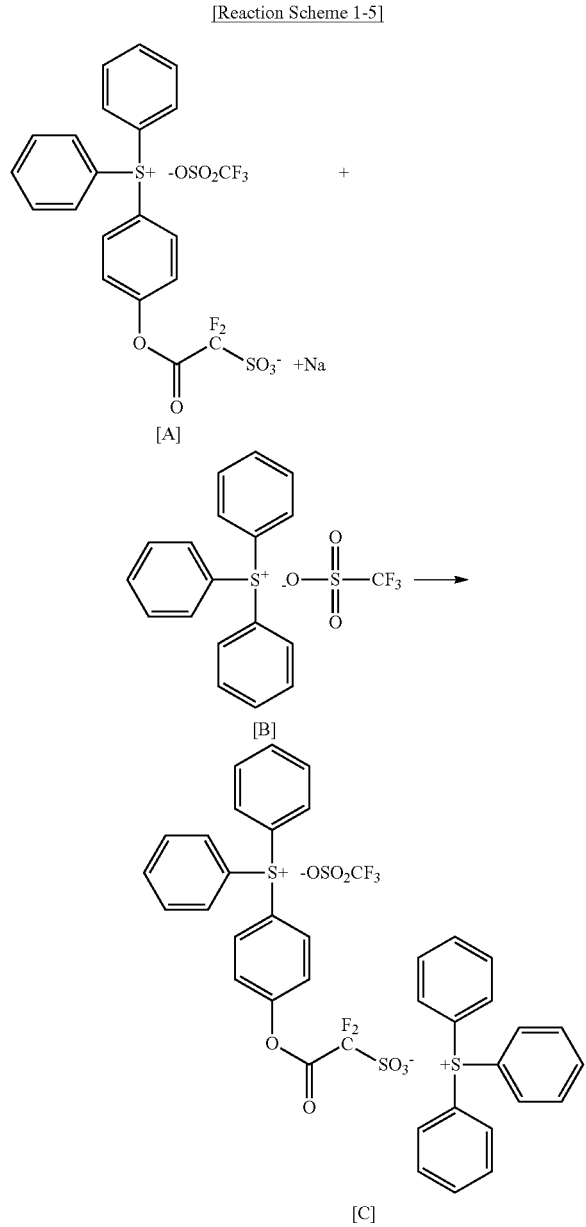

[Reaction Scheme 1-5]

sulfonate were dissolved in 200 ml of dichloromethane (MC) and 200 ml of distilled water (DW) to prepare a mixed solution, and the mixed solution was vigorously stirred for 5 hours at room temperature (about 25° C.). Thus, a reaction solution was prepared.

The completion point of the reaction of the reaction solution was confirmed by 19F-NMR, and after completion of the reaction, the reaction solution was washed with an aqueous solution of $K_2CO_3$ and distilled water. The organic layer was concentrated, and thus a reaction liquid was prepared. The crude reaction liquid was purified using dichloromethane and hexane, and from the purified reaction liquid, 62 g (yield 95%) of a compound represented by [C] in the following reaction scheme (2) was obtained.

Figure 2:
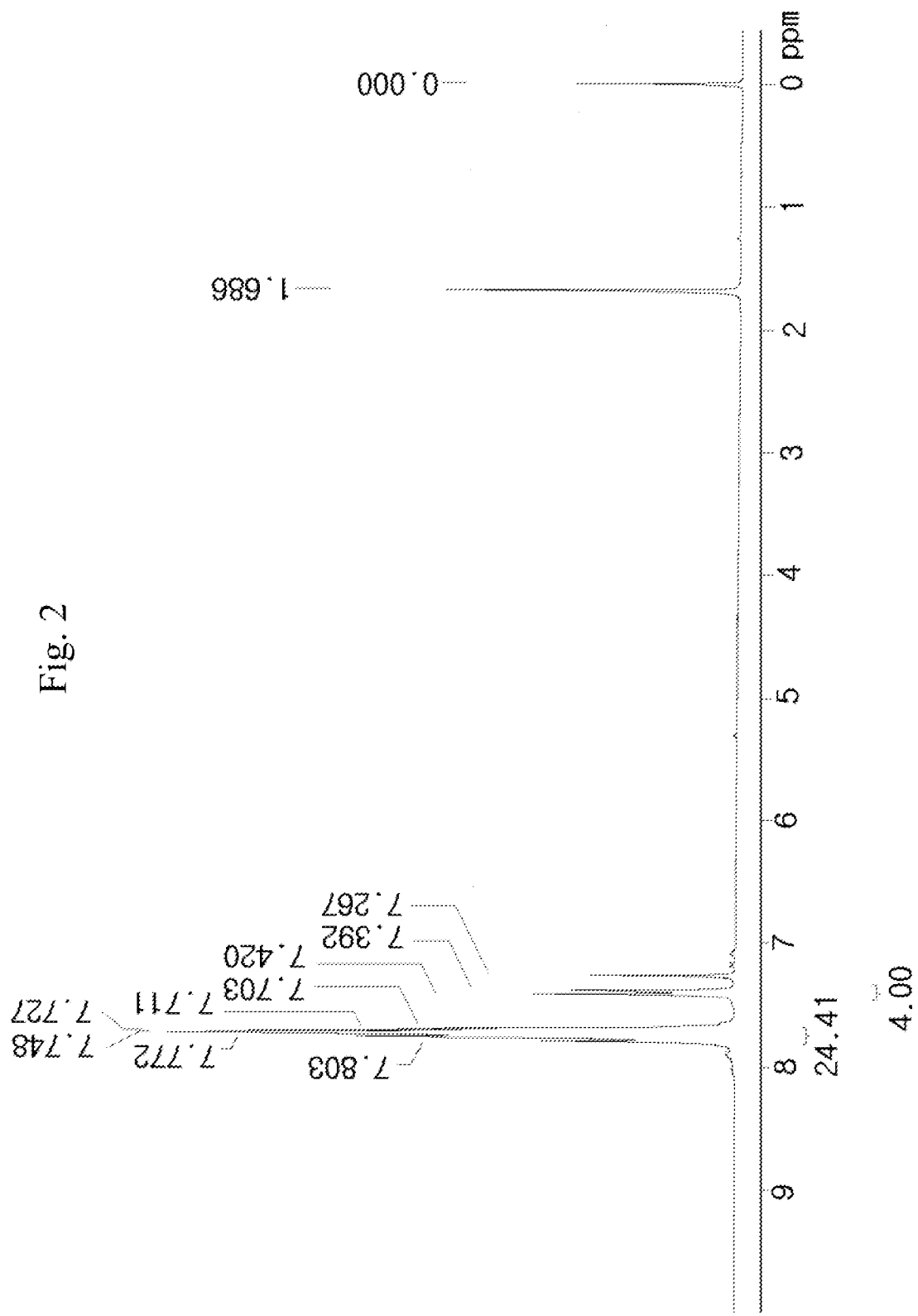
FIG. 2 is a graph showing the NMR data of compound [C] produced according to reaction scheme (2)

FIG. 2 presents the NMR data of the compound [C] produced by the reaction scheme (2).

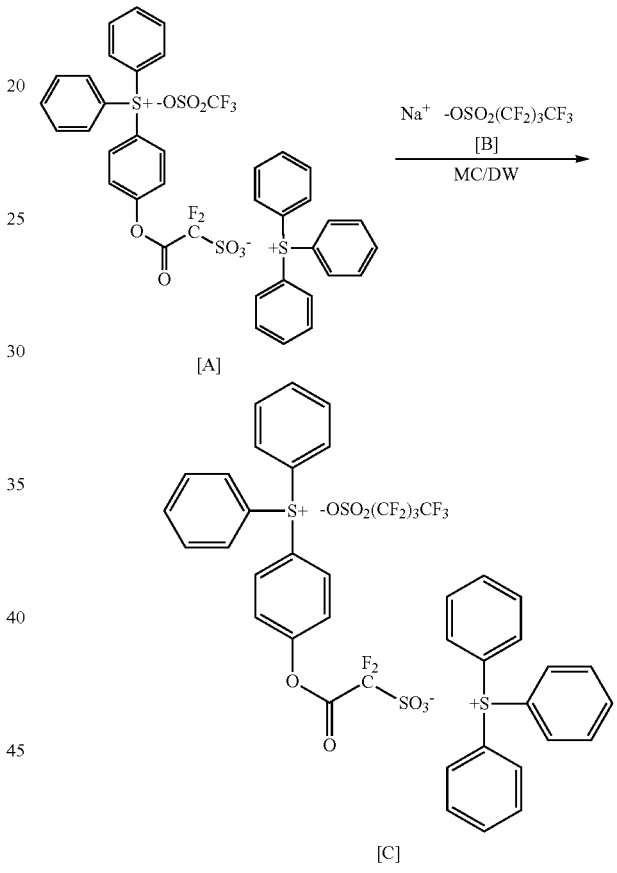

[Reaction Scheme 2]

Synthesis Example 3

50 g of a compound represented by [A] in the following reaction scheme (3) and 24.5 g of adamantane-1-carboxylic acid 2,2-difluoro-2-methanesulfonylethyl ester sodium salt represented by [B] in the following reaction scheme (3) were dissolved in 200 ml of dichloromethane (MC) and 200 ml of distilled water (DW) to prepare a mixed solution. The mixed solution was vigorously stirred for 5 hours at room temperature (about 25° C.), and thus a reaction solution was prepared.

The completion point of the reaction of the reaction solution was confirmed by $^{19}$F-NMR, and after completion of the reaction, the reaction solution was washed with an aqueous solution of $K_2CO_3$ and distilled water. The organic layer was concentrated, and thus a reaction liquid was prepared. The crude reaction liquid was purified using dichloromethane and hexane, and from the purified reaction liquid, 55.4 g (yield 92%) of a compound represented by [C] in the following reaction scheme (3) was obtained.

Synthesis Example 2

Figure 3:
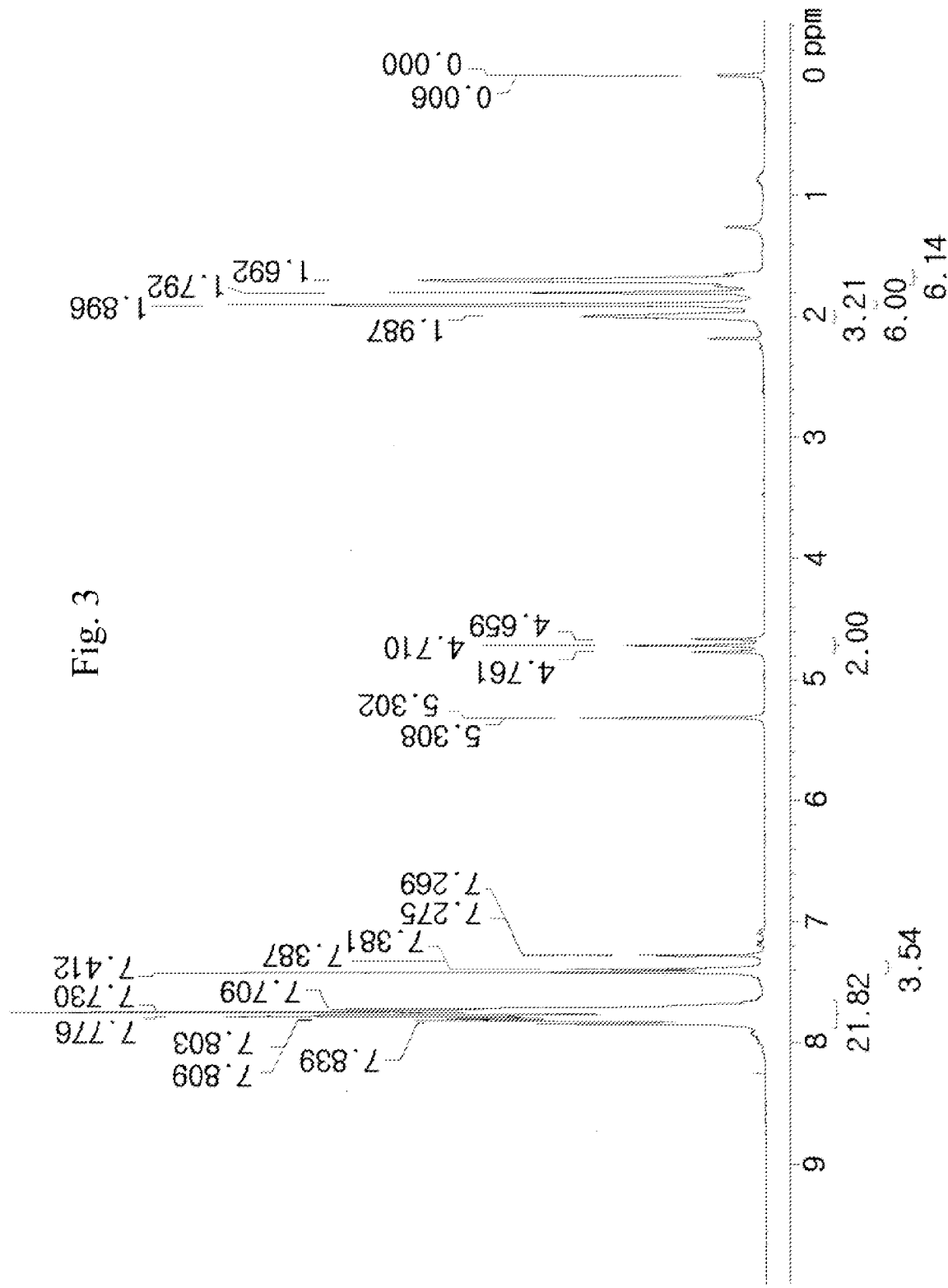
FIG. 3 is a graph showing the NMR data of compound [C] produced according to reaction scheme (3).

50 g of a compound represented by [A] in the following reaction scheme 2 and 23 g of sodium nonafluorobutane- FIG. 3 presents the NMR data of the compound [C] produced by the reaction scheme (3).

[Reaction Scheme 3]

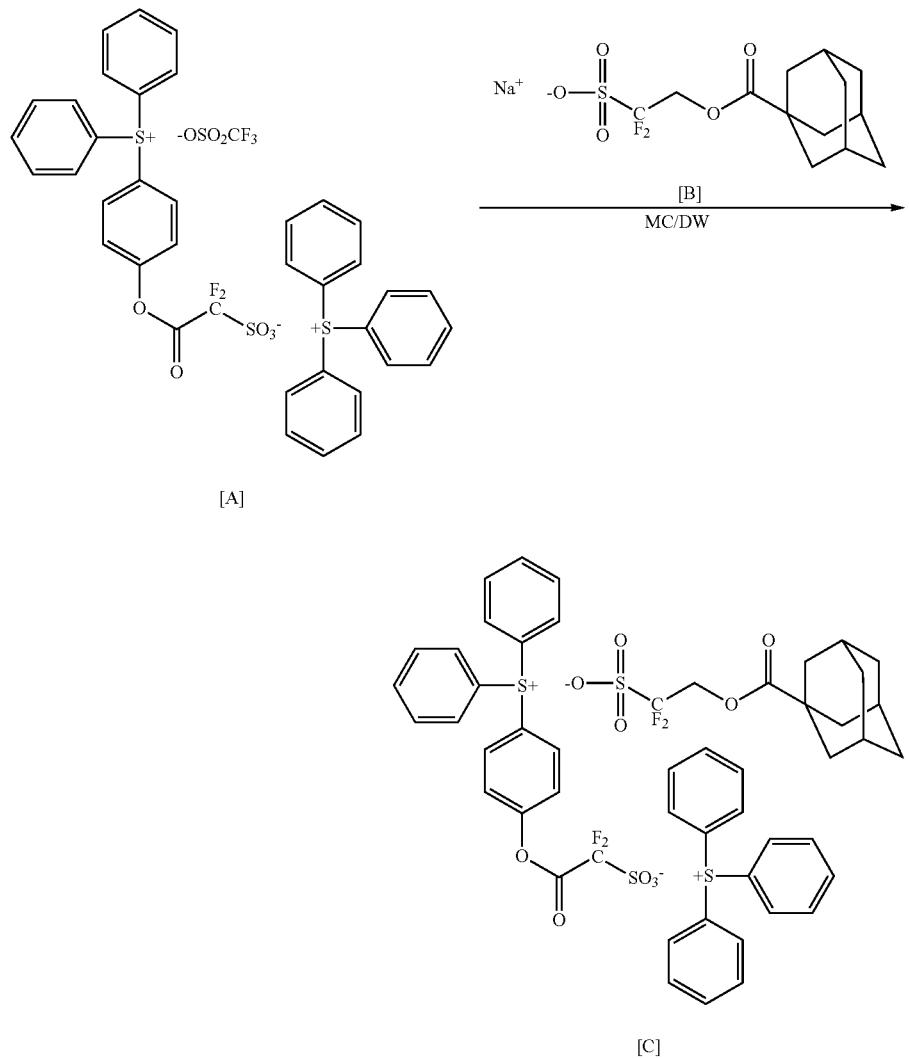

Synthesis Example for Resin

3-Bicyclo[2.2.1]hept-5-en-2-yl-3-hydroxypropionic acid t-butyl ester, 1-methyladamantane acrylate, and γ-butyrolactone methyl acrylate were introduced at a molar ratio of 1:1:1 (33 parts by mole:33 parts by mole:33 parts by mole), and 1,4-dioxane was used as a polymerization solvent in an amount three times the total mass of the reaction monomers. Azobisisobutyronitrile was incorporated as an initiator at a proportion of 4 mol % relative to the total molar amount of the monomers, and thus a mixed solution was prepared.

The mixed solution was allowed to react for 16 hours at 65° C. to prepare a reaction solution, and the reaction solution was precipitated in n-hexane and was dried in a vacuum. Thus, a resin represented by the following formula (1), which is a copolymer having a weight average molecular weight of about 8,500, was obtained.

[Chemical Formula 10]

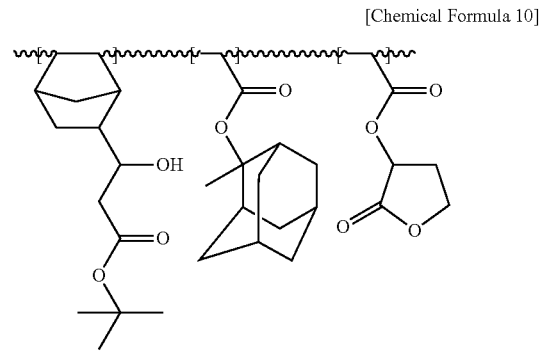

Preparation Example for Resist

A resist composition was prepared at the composition ratios indicated in the following Table 1, including 100 parts by weight of the copolymer represented by formula (10) obtained in the Synthesis Example for resin, and the like.

Specifically, in Example 1, 100 parts by weight of the copolymer of formula (10) obtained in the Synthesis Example for resin, 4 parts by weight of the compound represented by [C] in the reaction scheme (1-5) produced in the Synthesis Example 1 as an acid generator, and 0.5 parts by weight of tetramethylammonium hydroxide as a basic additive were dissolved in 1,000 parts by weight of propylene glycol methyl ether acetate. Subsequently, the solution was filtered through a 0.2-μm membrane filter, and thus a resist liquid was prepared.

The resist liquid was applied on a substrate using a spinner, and was dried for 90 seconds at 110° C. Thus, a coating film having a thickness of 0.20 μm was formed.

The coating film thus formed was exposed using an ArF excimer laser stepper (lens aperture number: 0.78), and then was heat treated for 90 seconds at 110° C.

The coating film was developed using a 2.38 wt % aqueous solution of tetramethylammonium hydroxide as a developer solution, and was washed and dried. Thus, a resist pattern was formed.

In Example 2, Example 3, Comparative Example 1 and Comparative Example 2, the method for preparing a resist liquid and the method for forming a pattern were applied in the same manner as in Example 1, except that only the photoacid generators of specified types in the following Table 1 were applied.

TABLE 1

|  | Resin (100 parts by weight) | *PAG (parts by weight) | *Base (parts by weight) |
|---|---|---|---|
| Example 1 | Copolymer of formula (10) | Formula A (4.0) | 0.5 |
| Example 2 | Copolymer of formula (10) | Formula B (4.0) | 0.5 |
| Example 3 | Copolymer of formula (10) | Formula C (4.0) | 0.5 |
| Comparative Example 1 | Copolymer of formula (10) | Triphenylsulfonium triflate (4.0) | 0.5 |
| Comparative Example 2 | Copolymer of formula (10) | Triphenylsulfonium triflate (2.0) Formula D (2.0) | 0.5 |

*Type of PAG used in Table 1

[Chemical Formula 4]

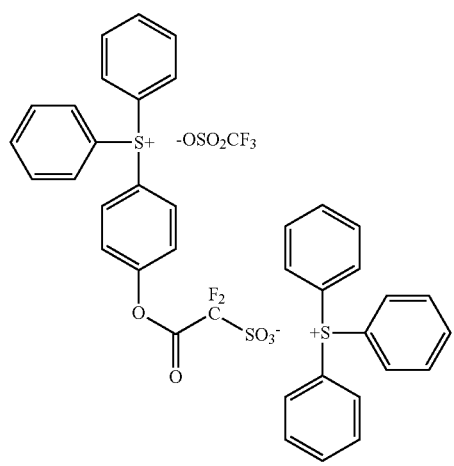

[Chemical Formula B]

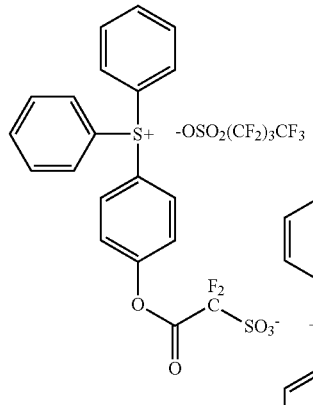

[Chemical Formula C]

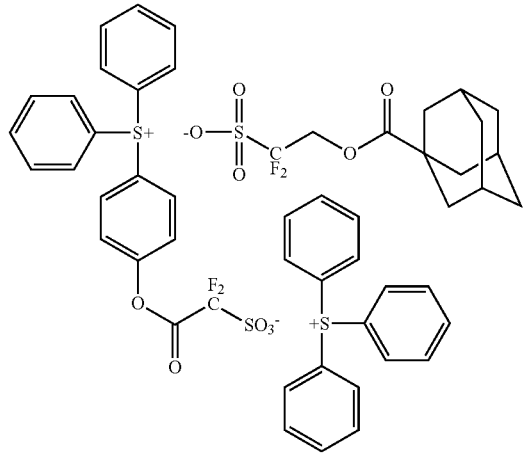

[Chemical Formula D]

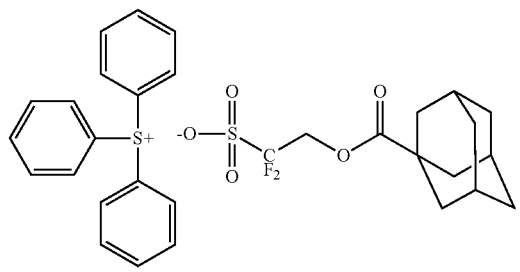

Evaluation of Properties

The results for the formation of resist patterns were evaluated by the method described below, and the evaluation results are presented in the following Table 2.

In regard to the sensitivity, the amount of exposure required to form a 0.10-μm line-and-space (L/S) pattern at a line width of 1:1 after development is designated as the optimum amount of exposure, and this optimum amount of exposure is presented as sensitivity.

In regard to the resolution, the minimum pattern dimension resolved by the optimum amount of exposure is designated as the resolution.

In regard to the LER, the roughness of the pattern was observed in the 0.10-μm line-and-space (L/S) pattern formed after development, and the LER was measured (a smaller number represents a superior LER).

TABLE 2

|  | Sensitivity (mJ/cm2) | Resolution (nm) | LER |
|---|---|---|---|
| Example 1 | 12 | 80 | 4 |
| Example 2 | 13 | 80 | 3 |
| Example 3 | 14 | 70 | 3 |
| Comparative Example 1 | 17 | 100 | 7 |
| Comparative Example 2 | 16 | 90 | 6 |

According to the Table 2, it can be seen that Examples 1 to 3 of the present invention exhibit enhanced results in all of the sensitivity, resolution and line edge roughness (LER).

Furthermore, as compared with Comparative Example 2 in which a mixture of triphenylsulfonium triflate and the compound of formula (D) was applied, Examples 1 to 3 exhibited superior results in all of the sensitivity, resolution and LER, and especially, Example 3 exhibited particularly excellent results in terms of the resolution and LER.

Preferred embodiments of the present invention have been described in detail in the above, but the scope of the invention is not limited to the specific details and representative embodiments shown and described herein. Accordingly, various modifications may be made without departing from the spirit or scope of the general inventive concept as defined by the appended claims and their equivalents.

The invention claimed is:

1. A sulfonium compound having two acid sites, each respectively having an acid generator that is different from the other, and represented by the following formula (1):

[Chemical Formula 1]

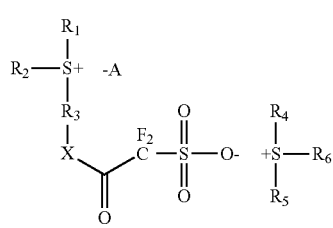

wherein in the formula (1),

X represents an electron donor group;

$R_1$ and $R_2$ each independently represent any one selected from the group consisting of an alkyl group, a cycloalkyl group, an aryl group, a heteroalkyl group, a heterocycloalkyl group and a heteroaryl group, or $R_1$ and $R_2$ may be joined, together with the sulfur atom to which $R_1$ is bonded, to form a heterocycloalkyl group having 2 to 7 carbon atoms;

$R_4$ to $R_6$ each independently represent any one selected from the group consisting of an alkyl group, a cycloalkyl group, an aryl group, a heteroalkyl group, a heterocycloalkyl group, and a heteroaryl group, or $R_4$ and $R_5$ may be joined, together with the sulfur atom to which $R_4$ is bonded, to form a heterocycloalkyl group having 2 to 7 carbon atoms;

$R_3$ represents any one selected from the group consisting of a cyclic alkenediyl group, a heterocyclic alkenediyl group, an arylene group and a heteroarylene group; and A represents an anion.

2. The sulfonium compound according to claim 1, wherein A represents any one of the group consisting of a sulfonate anion, an imide anion, a methide anion, a halogenated alkyl anion, a carboxylate anion, an iodonium anion and a sulfonylimide anion.

3. The sulfonium compound according to claim 1, wherein −A represents any one selected from the group consisting of anions represented by the following formula (1-1), (1-2) and (1-3):

[Chemical Formula 1-1]

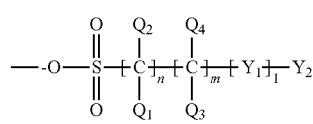

wherein in the formula (1-1), $Q_1$, $Q_2$, $Q_3$ and $Q_4$ each independently represent any one selected from the group consisting of a hydrogen atom, a halogen atom and an alkyl group;

$Y_1$ represents any one selected from the group consisting of an alkanediyl, an alkenediyl, NR', S, O, CO and combinations thereof, R' represents any one selected from the group consisting of a hydrogen atom and an alkyl group;

$Y_2$ represents any one selected from the group consisting of a hydrogen atom, an alkyl group, a cycloalkyl group, a heterocycloalkyl group, an aryl group, a heteroaryl group, a heteroalkyl group, an allyl group, a perfluoroalkyl group, a haloalkyl group, and an alkylsulfonyl group;

n represents an integer from 0 to 10, m represents an integer from 0 to 10, and l represents an integer from 0 to 5;

[Chemical Formula 1-2]

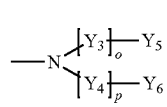

wherein in the formula (1-2), $Y_3$ and $Y_4$ each independently represent any one selected from the group consisting of an alkanediyl, an alkenediyl, NR', S, O, CO, $O_2$S and combinations thereof, R' represents any one selected from the group consisting of a hydrogen atom and an alkyl group;

$Y_5$ and $Y_6$ each independently represent any one selected from the group consisting of a hydrogen atom, an alkyl group, a cycloalkyl group, a heterocycloalkyl group, an aryl group, a heteroaryl group, a heteroalkyl group, an allyl group, a perfluoroalkyl group, a haloalkyl group, and an alkylsulfonyl group;

o represents an integer from 0 to 5, and p represents an integer from 0 to 5; and

[Chemical Formula 1-3]

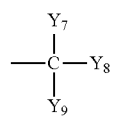

wherein in the formula (1-3), $Y_7$, $Y_8$ and $Y_9$ each independently represent any one selected from the group consisting of a hydrogen atom, an alkyl group, a cycloalkyl group, a heterocycloalkyl group, an aryl group, a heteroaryl group, a heteroalkyl group, an allyl group, a perfluoroalkyl group, a haloalkyl group and an alkylsulfonyl group.

4. The sulfonium compound according to claim 1, wherein –A represents any one selected from the group consisting of —$OSO_2CF_3$, —$OSO_2C_4F_9$, —$OSO_2C_8F_{17}$, —$N(CF_3)_2$, —$N(C_2F_5)_2$, —$N(C_4F_9)_2$, —$C(CF_3)_3$, —$C(C_2F_5)_3$, —$C(C_4F_9)_3$ and an anion represented by the following formula (1-4):

[Chemical Formula 1-4]

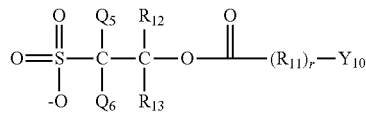

wherein in the formula (1-4),
- $Y_{10}$ represents any one selected from the group consisting of a cycloalkyl group, a heterocycloalkyl group, an aryl group, a heteroaryl group, an alkyl group, a heteroalkyl group, an allyl group, a perfluoroalkyl group, a haloalkyl group and an alkylsulfonyl group;
- $R_{11}$ represents any one selected from the group consisting of an alkanediyl, an alkenediyl, NR', S, O, CO and combinations thereof, R' represents any one selected from the group consisting of a hydrogen atom and an alkyl group;
- $R_{12}$ and $R_{13}$ each independently represent any one selected from the group consisting of a hydrogen atom and an alkyl group having 1 to 8 carbon atoms;
- r represents an integer from 0 to 5; and
- $Q_5$ and $Q_6$ each independently represent a halogen atom.

5. The sulfonium compound according to claim 1, wherein $R_3$ represents any one selected from the group consisting of groups represented by the following formulas (2-1) to (2-4):

[Chemical Formula 2-1]

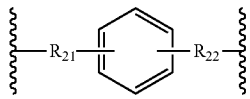

[Chemical Formula 2-2]

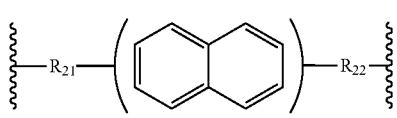

[Chemical Formula 2-3]

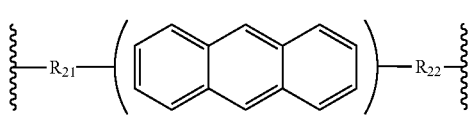

[Chemical Formula 2-4]

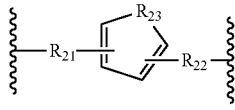

wherein in the formulas (2-1) to (2-4),
- $R_{21}$ and $R_{22}$ each independently represent any one selected from the group consisting of a single bond, an alkanediyl having 1 to 5 carbon atoms, and an alkenediyl having 2 to 5 carbon atoms; and
- $R_{23}$ represents any one selected from the group consisting of —$CH_2$—, —O— and —S—.

6. The sulfonium compound according to claim 1, wherein X represents any one selected from the group consisting of —O—, —S—, —O—$(CH_2)_n$—O— (wherein n represents an integer from 1 to 5), —$(CH_2)_n$—S— (wherein n represents an integer from 1 to 5), and a group represented by the following formula (3-1):

[Chemical Formula 3-1]

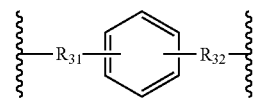

wherein in the formula (3-1),
- $R_{31}$ and $R_{32}$ each independently represent any one selected from the group consisting of —O—, —S— and combinations thereof.

7. The sulfonium compound according to claim 1, wherein the sulfonium compound represented by the formula (1) is any one selected from the group consisting of compounds represented by the following formula (5-1) to formula (5-3):

[Chemical Formula 5-1]

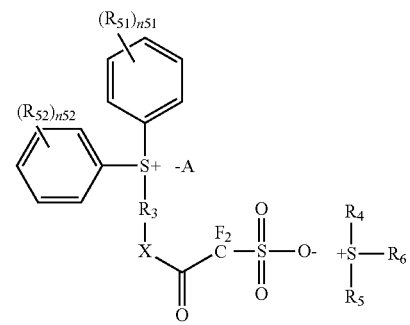

[Chemical Formula 5-2]

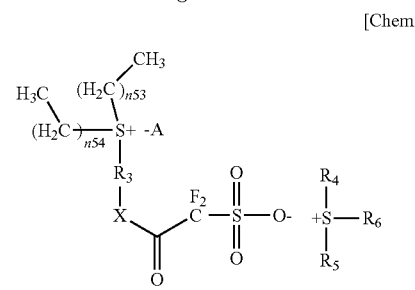

[Chemical Formula 5-3]

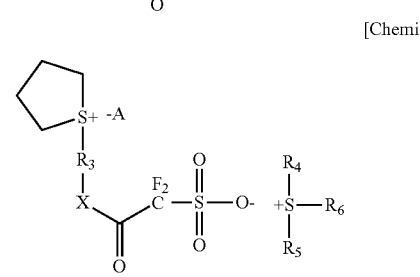

wherein in the formulas (5-1) to (5-3),
- $R_{51}$ and $R_{52}$ each independently represent any one selected from the group consisting of a hydrogen atom, an alkyl group having 1 to 5 carbon atoms, and a halogenated alkyl group having 1 to 5 carbon atoms;
- n51 and n52 each independently represent an integer from 1 to 5;

n53 and n54 each independently represent an integer from 0 to 10;

$R_3$ represents any one selected from the group consisting of a cycloalkenediyl group, a heterocyclic alkenediyl group, an arylene group and a heteroarylene group;

X represents an electron donor group;

$R_4$ to $R_6$ each independently represent any one selected from the group consisting of an alkyl group, a cycloalkyl group, an aryl group, a heteroalkyl group, a heterocycloalkyl group, and a heteroaryl group, or $R_4$ and $R_5$ may be joined, together with the sulfur atom to which $R_4$ is bonded, to form a heterocycloalkyl group having 2 to 7 carbon atoms; and −A represents an anion.

* * * * *